(12) United States Patent
Sauer

(10) Patent No.: US 11,490,926 B2
(45) Date of Patent: Nov. 8, 2022

(54) DEVICE FOR PACEMAKER LEAD PLACEMENT AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 948 days.

(21) Appl. No.: 16/209,362

(22) Filed: Dec. 4, 2018

(65) Prior Publication Data

US 2019/0126035 A1 May 2, 2019

Related U.S. Application Data

(63) Continuation-in-part of application No. 15/831,121, filed on Dec. 4, 2017, now abandoned.

(60) Provisional application No. 62/429,679, filed on Dec. 2, 2016.

(51) Int. Cl.
| | |
|---|---|
| *A61B 17/34* | (2006.01) |
| *A61N 1/05* | (2006.01) |
| *A61B 17/04* | (2006.01) |
| *A61N 1/362* | (2006.01) |
| *A61B 17/06* | (2006.01) |
| *A61B 17/00* | (2006.01) |

(52) U.S. Cl.
CPC ...... *A61B 17/3468* (2013.01); *A61B 17/0469* (2013.01); *A61N 1/059* (2013.01); *A61N 1/0592* (2013.01); *A61N 1/362* (2013.01); *A61B 17/06061* (2013.01); *A61B 17/3417* (2013.01); *A61B 2017/00738* (2013.01); *A61B 2017/0608* (2013.01)

(58) Field of Classification Search
CPC ............ A61B 17/0469; A61B 17/0482; A61B 17/0483; A61B 17/0485; A61B 17/0491; A61B 17/3468; A61B 2017/0472; A61N 1/05; A61N 1/37518; A61N 1/059
See application file for complete search history.

(56) References Cited

U.S. PATENT DOCUMENTS

| | | | |
|---|---|---|---|
| 5,158,097 A | * | 10/1992 | Christlieb ............ A61N 1/0587 600/377 |
| 6,360,130 B1 | | 3/2002 | Duysens et al. |
| 6,941,174 B2 | | 9/2005 | Shchervinsky |

(Continued)

FOREIGN PATENT DOCUMENTS

| | | |
|---|---|---|
| EP | 873155 | 6/2003 |
| EP | 815897 | 12/2004 |

(Continued)

*Primary Examiner* — Sarah W Aleman
(74) *Attorney, Agent, or Firm* — Michael E. Coyne; Christopher Miller

(57) ABSTRACT

A device for pacemaker lead placement is disclosed. The device has a device tip having a tissue bite area, ferrule holders, and needle tips. The device also has a lead end rest at the distal end, with a pacemaker lead end situated on the lead end rest, the pacemaker lead end having first and second anchor suture holes. The device further has an anchor suture with ferrules at respective ends of the anchor suture, wherein the ferrules of the anchor suture are passed through the anchor suture holes and into communication with the ferrule holders. The device further has one or more tube guides configured to organize and manage sutures during a minimally invasive surgical procedure.

10 Claims, 26 Drawing Sheets

(56) References Cited

U.S. PATENT DOCUMENTS

| | | |
|---|---|---|
| 7,418,298 B2 | 8/2008 | Shiroff et al. |
| 7,499,759 B2 | 3/2009 | Coe |
| 8,532,791 B2 | 9/2013 | Wanna |
| 9,220,891 B2 | 12/2015 | Osypka |
| 2003/0216613 A1* | 11/2003 | Suzuki .................. A61B 50/13 600/104 |
| 2016/0345959 A1* | 12/2016 | Sauer ............... A61B 17/06004 |

FOREIGN PATENT DOCUMENTS

| | | | | |
|---|---|---|---|---|
| GB | 2025236 | * | 1/1980 | ......... A61B 17/0469 |
| WO | WO1997025099 | | 7/1997 | |

* cited by examiner

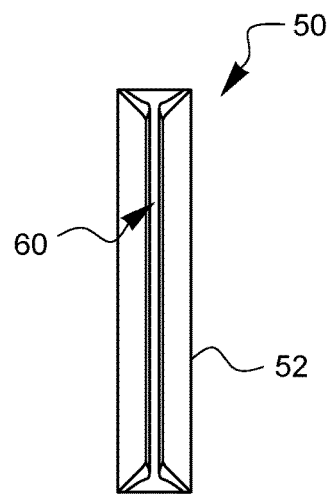
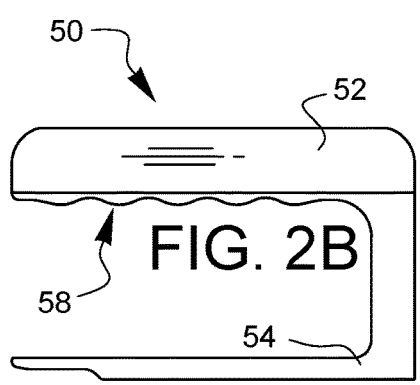
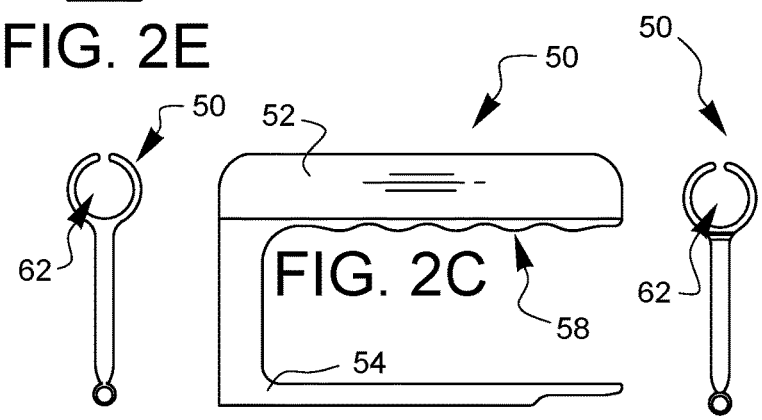
FIG. 2E
FIG. 2B    FIG. 2A    FIG. 2C    FIG. 2D
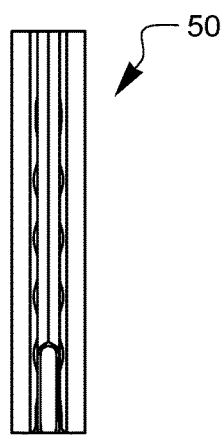
FIG. 2F

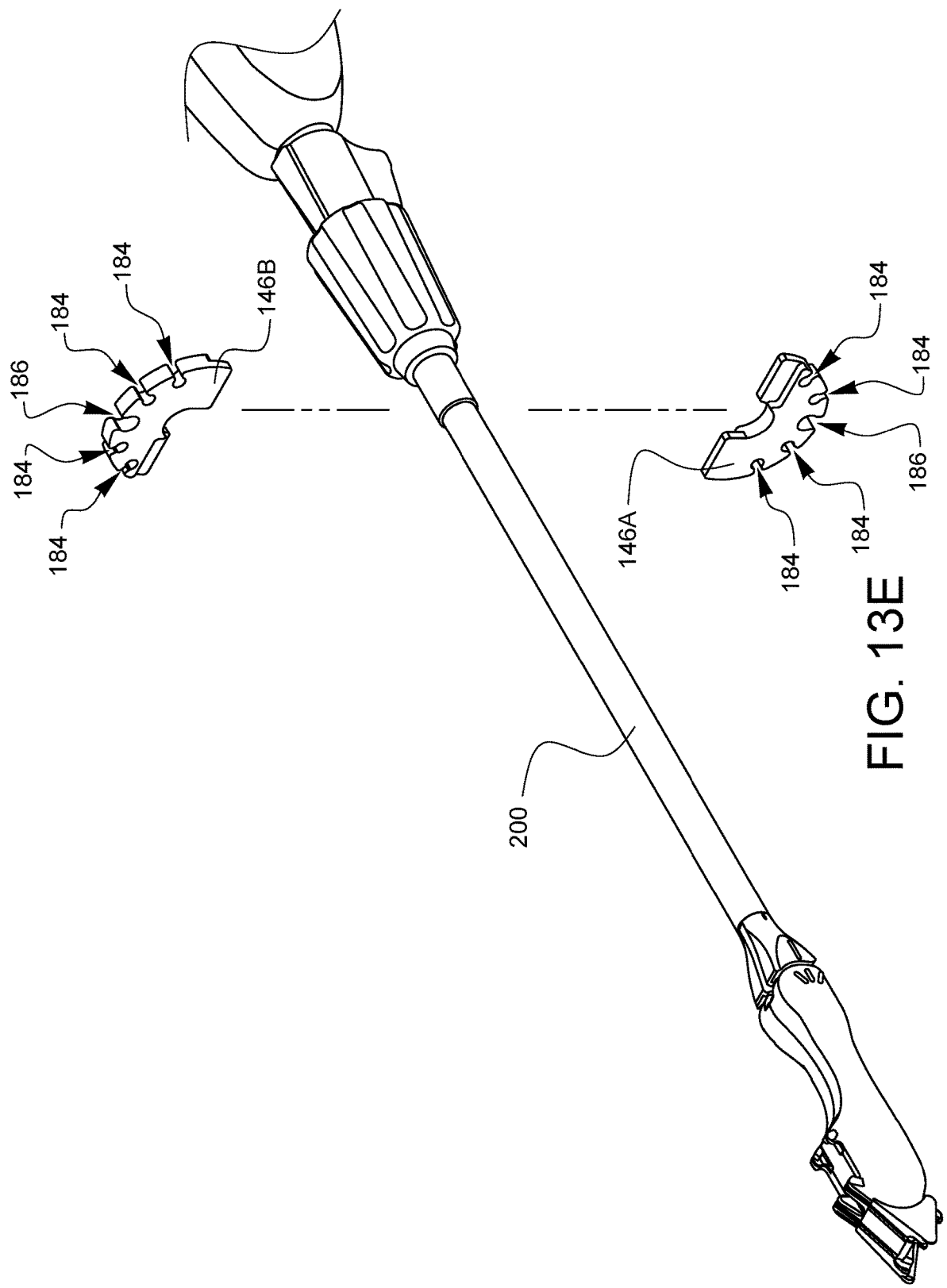

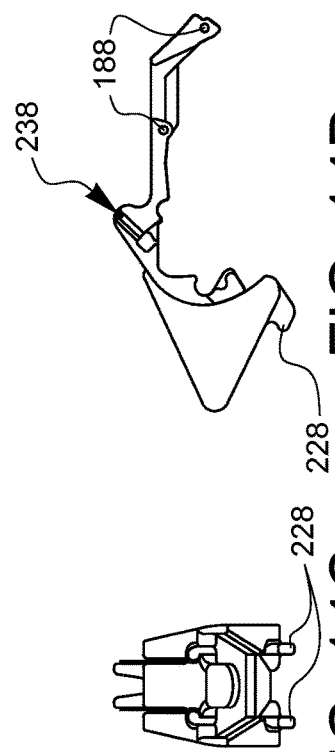
FIG. 14D
FIG. 14C
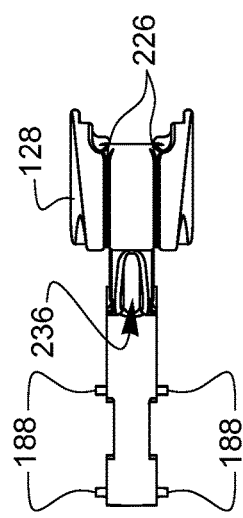
FIG. 14E
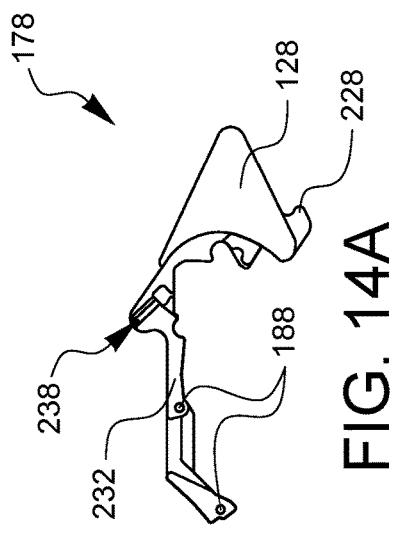
FIG. 14A
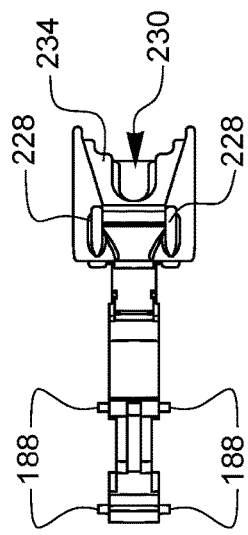
FIG. 14F
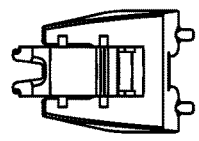
FIG. 14B

DEVICE FOR PACEMAKER LEAD PLACEMENT AND METHODS THEREOF

RELATED APPLICATION

This application is a continuation-in-part of U.S. Non-Provisional patent application Ser. No. 15/831,121 filed Dec. 4, 2017 and entitled, "DEVICE FOR PEDIATRIC LEAD PLACEMENT AND METHODS THEREOF". The Ser. No. 15/831,121 application is hereby incorporated by reference in its entirety. The Ser. No. 15/831,121 application claims priority to U.S. Provisional Patent Application No. 62/429,679 filed Dec. 2, 2016 and entitled, "DEVICE FOR PEDIATRIC LEAD PLACEMENT AND METHODS THEREOF". The Ser. No. 15/831,121 and 62/429,679 applications are hereby incorporated by reference in its entirety.

FIELD

The claimed invention relates to surgical devices, and more specifically to surgical devices which may be used for the placement of a pacemaker lead onto the heart of a pediatric patient using minimally invasive surgical techniques.

BACKGROUND

Pacemaker therapy in children involves unique issues regarding patient size, growth, development, and possible presence of congenital heart disease. Traditionally, pacing leads can be implanted via the transvenous (endocardial) or surgical (epicardial) route. The choice of route has been dependent upon the size of the patient, anatomy, and surgical procedures performed that can affect the access to certain cardiac structures.

Traditionally, epicardial lead placement has been recommended in patients less than 15 kg, patients with intracardiac shunt lesions, patients with limited access to the atrium or the ventricle (e.g. patients with single ventricular physiology post Fontan palliation), and patients with prosthetic tricuspid valves. Traditionally, epicardial lead implantation has required a sternotomy or thoracotomy or subxiphoid approach, and is associated with higher chronic stimulation threshold, higher lead failures and fractures, and early depletion of battery life. However, it preserves the venous access for future use.

Endocardial (Transvenous route) lead implantation has been preferred in most pediatric patients except for those situations referred above. Endocardial lead placement has offered the advantages of avoidance of thoracotomy, lower pacing thresholds, and a lower incidence of lead fractures. However, its disadvantages include a greater risk of lead dislodgment, venous occlusion, embolic vascular events, and endocarditis.

It would be desirable to have an effective, easy to use device for pediatric lead placement that avoids both the need for a sternotomy/thoracotomy while also avoiding endocardial lead placement entirely.

SUMMARY

A surgical device for pacemaker lead placement is disclosed, including a device tip having a tissue bite area, ferrule holders, and needle tips. The surgical device for pacemaker lead placement also has a lead end rest on a distal end of the device tip, a pacemaker lead end situated on the lead end rest, the pacemaker lead end having first and second anchor suture holes. The surgical device for lead placement includes an anchor suture with ferrules at respective ends of the anchor suture, where the ferrules of the anchor suture are passed through the anchor suture holes and into communication with the ferrule holders.

The surgical device for pacemaker lead placement further includes a recess on the lead end, configured to releasably hold a pacemaker lead end. The device may include a second pacemaker lead.

A method of placing a pacemaker lead end placement is also disclosed, including placing an incision below a xiphoid and above a diaphragm of a patient, and inserting a pediatric scope port into the incision towards a pericardium of the patient. The disclosed method further includes placing an anchor suture in a heart, routing one or more ends of the anchor suture through one or more anchor suture holes in a pacemaker lead end, attaching a first coupling suture to the pacemaker lead end at a proximal position on the pacemaker lead end, and aligning and securing a first end of the anchor suture to the first coupling suture.

BRIEF DESCRIPTION OF THE DRAWINGS

FIGS. 2A, 2B, 2C, 2D, 2E, and 2F are front (proximal side), left, right, rear (distal side), top, and bottom elevational views, respectively of the pediatric scope port of FIGS. 1A-1C.

FIGS. 13B-13E are exploded views illustrating assembly of a distal end of the embodiment of the minimally invasive surgical suturing device of FIG. 13A.

FIGS. 14A, 14B, 14C, 14D, 14E, 14F are front, left, right, rear, top, and bottom elevation views, respectively, of the lead end rest assembly of the surgical suturing device of FIGS. 13A-13F.

DETAILED DESCRIPTION

Figure 1A:
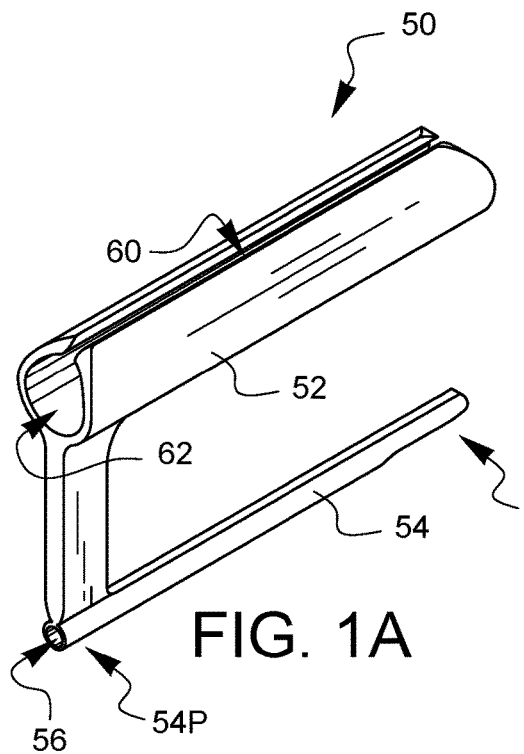
FIGS. 1A-1C are different perspective views of one embodiment of a pediatric scope port.
Figure 1B:
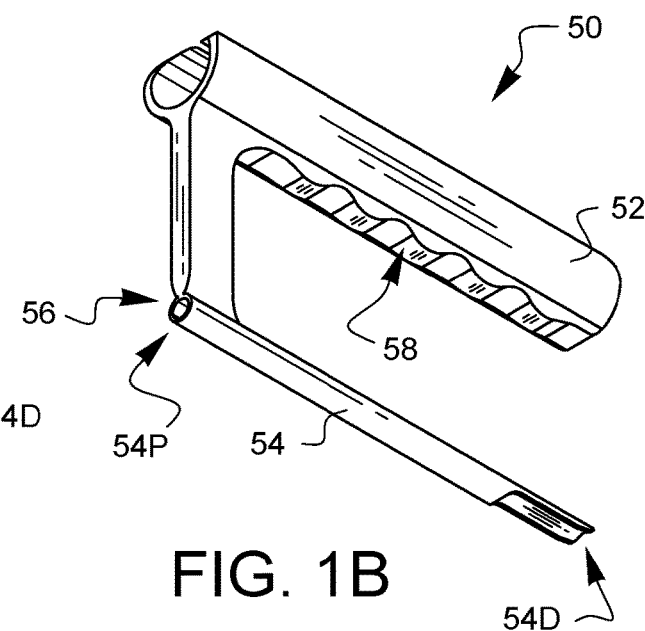
Figure 1C:
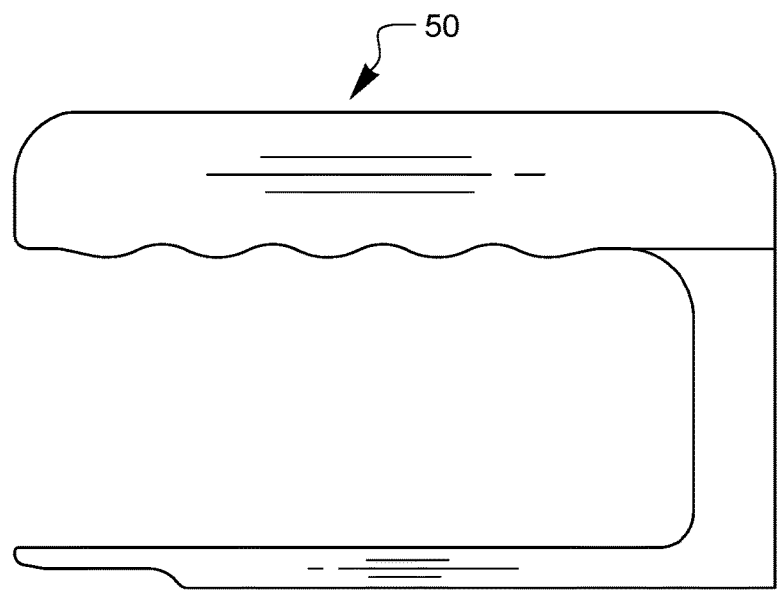

The devices and methods disclosed herein contemplate one or more ports as part of a pediatric lead system. One such port could be a pediatric scope port 50, such as the one shown in top and bottom perspective views (FIGS. 1A and 1B) as well as in a side view in FIG. 1C.

The pediatric scope port 50 has a handle 52 coupled to and spaced from a scope port cannula 54. The scope cannula 54 has a proximal end 54P and a distal end 54D. The handle 52 is coupled to the proximal end 54P of the scope cannula. An endoscopic viewing scope or the like may be introduced through a proximal opening 56 in the scope port cannula 54. The handle 52 may have a grip surface 58 to facilitate holding by a hand. The handle 52 may also have a cable access slot 60 which leads to an open handle interior 62. Cables from a viewing scope, such as the light source cable and/or the imaging cable, may be routed into the open handle interior 62 via the cable access slot 60 for efficient cable management as desired.

FIGS. 2A, 2B, 2C, 2D, 2E, and 2F are front (proximal side), left, right, rear (distal side), top, and bottom elevational views, respectively of the pediatric scope port 50.

Figure 3:
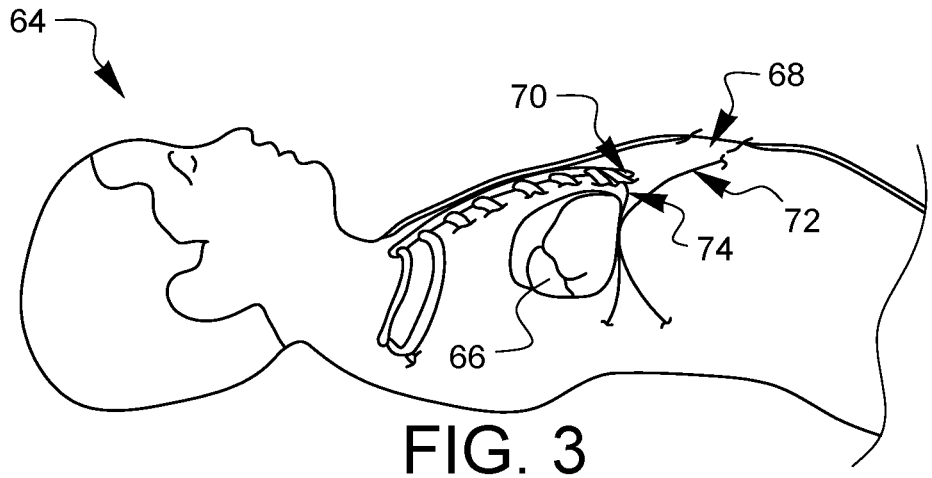
FIG. 3 schematically illustrates a patient with a heart in need of pacemaker lead placement.

Consider FIG. 3 which offers a schematic side view of a patient 64 with a heart 66 in need of pacemaker lead placement. A small incision 68 is made below the xiphoid 70 and above the diaphragm 72. If desired, a finger may be used to explore into this incision in order to create a channel towards the pericardium 74, just below the xiphoid 70.

Figure 4:
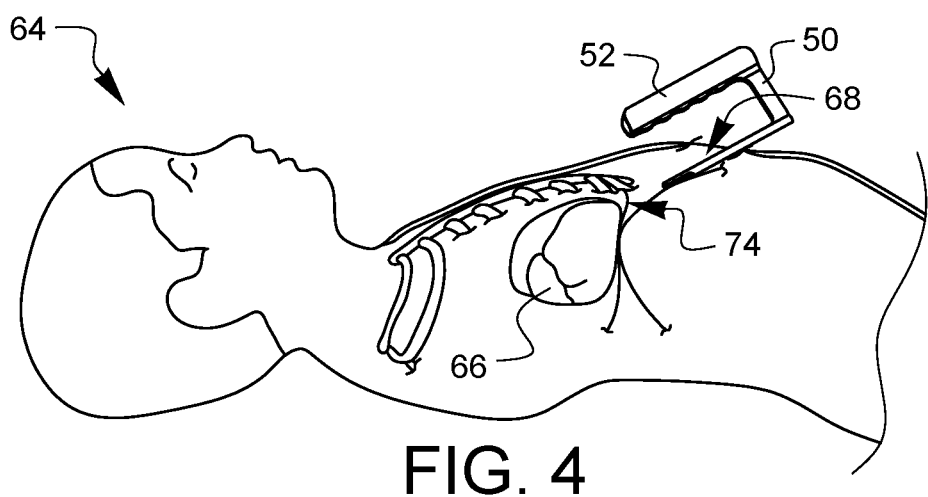
FIG. 4 schematically illustrates the pediatric scope port of FIGS. 1A-1C being slid into an incision towards the pericardium of the patient from FIG. 3.

The pediatric scope port 50 may be slid into the small incision 68 towards the pericardium 74 as illustrated schematically in FIG. 4.

Figure 5:
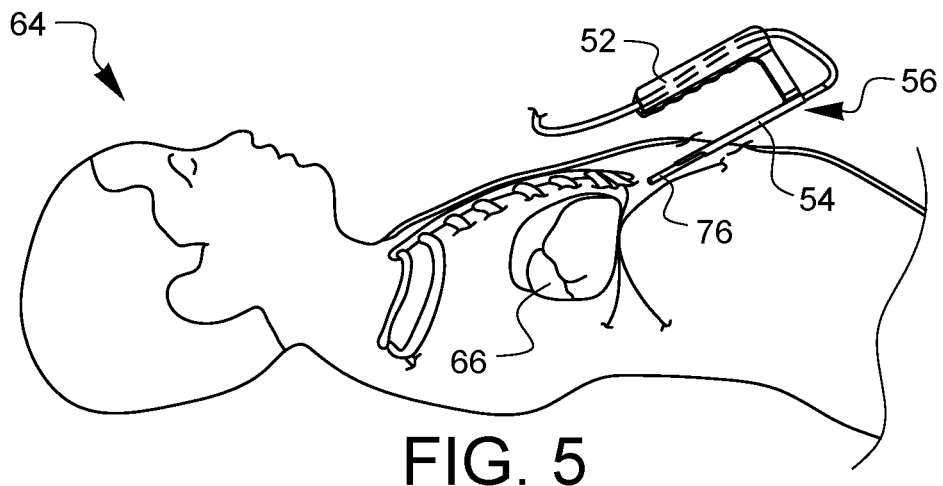
FIG. 5 schematically illustrates a viewing scope inserted into an opening of a scope port cannula in the pediatric scope port of FIG. 4.

A viewing scope 76 may be inserted into the proximal opening 56 in the scope port cannula 54 to provide the surgeon with a view of the channel leading to the pericardium 74 as well as the pericardium 74 itself as schematically illustrated in FIG. 5.

Minimally invasive surgical tools may also be introduced into the incision in order to create an opening in the pericardium, thereby exposing the heart without the need for a sternotomy, a thoracotomy, or endocardial methods. As desired, the handle 52 on the pediatric scope port 50 may be used by a surgical assistant to pull in an anterior direction. This will cause the top side of the scope port cannula 54 to pull tissue above the scope cannula in an anterior direction, thereby opening up the access passage as needed for other instruments.

Figure 6:
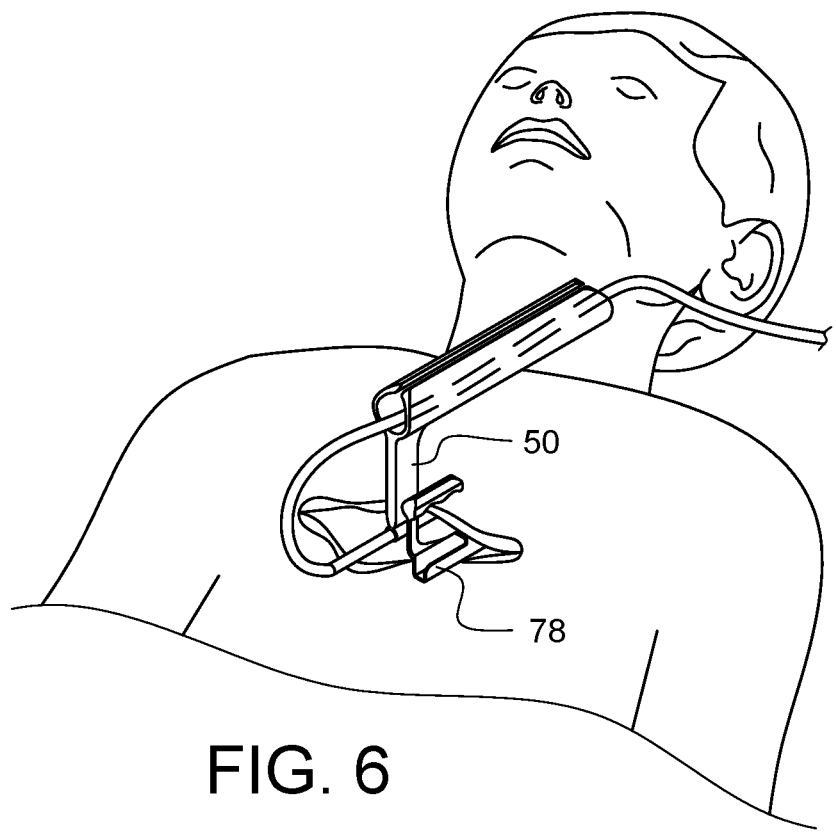
FIG. 6 schematically illustrates the embodied pediatric lead port of FIGS. 11A-11C inserted into a patient incision along with the pediatric scope port of FIG. 4.
Figure 7:
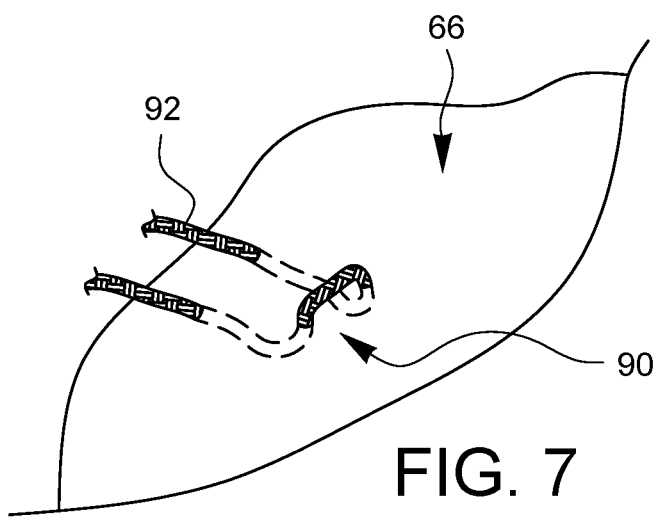
FIG. 7 illustrates one embodiment of a horizontal mattress suture stitch.

FIG. 6 schematically illustrates a pediatric scope port 50 and the pediatric lead cannula 78 installed in the incision. A horizontal mattress suture stitch 90, or a whatever stitch desired and deemed appropriate by the surgeon, will need to be made in the heart 66 where the pediatric lead is desired to be placed. The stitch 90 is made with suture 92. FIG. 7 schematically illustrates this type of stitch 90. This can be done with a needle driver or preferably with an automated suturing tool.

Figure 8A:
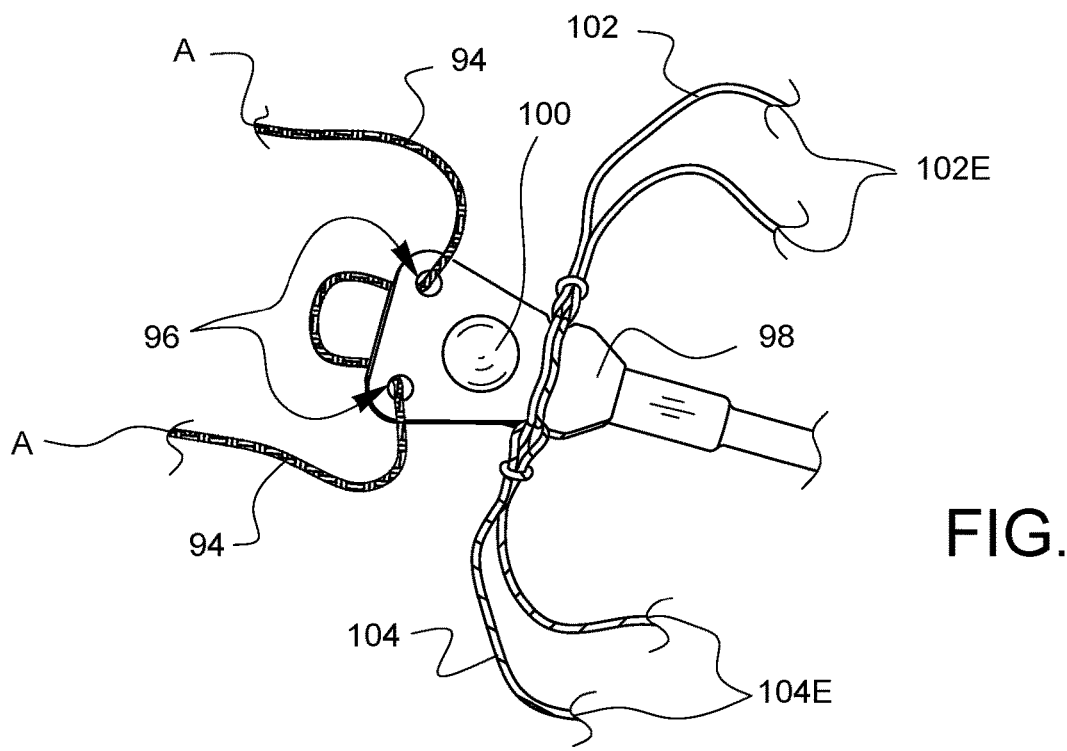
FIG. 8A illustrates a bottom view one embodiment of a pediatric pacemaker lead end having an anchoring suture and first and second coupling sutures.

The suture used to make this stitch in the heart may be called the anchor suture 94, and its ends should be routed as shown in FIG. 8A through anchor suture holes 96 in the pacemaker lead end 98. In this embodiment, the anchor suture holes 96 are located distally when compared to the lead electrode 100 on the pacemaker lead end 98. The lead electrode 100 is the portion of the pacemaker lead which will need to make good contact with the heart.

As shown in FIG. 8A, a first coupling suture 102 is coupled to the lead end 98 at a position proximal to the lead electrode 100. A second coupling suture 104 is also coupled to the lead end 98 at a position proximal to the lead electrode 100. In our embodiment, the first and second coupling sutures 102, 104 are colored differently and the first coupling suture 102 points in one direction while the second coupling suture 104 points in a substantially opposite direction. In this embodiment, the first coupling suture 102 was attached by knotting it to the lead end 98. Similarly, the second coupling suture 104 was attached by knotting it to the lead end 98. As a result, the first coupling suture 102 has two suture ends 102E which extend from the lead end 98. Similarly, the second coupling suture 104 has two suture ends 104E which extend from the lead end 98. Preferably, the anchor suture 94 is a different color from either of the coupling sutures 102, 104.

Figure 8B:
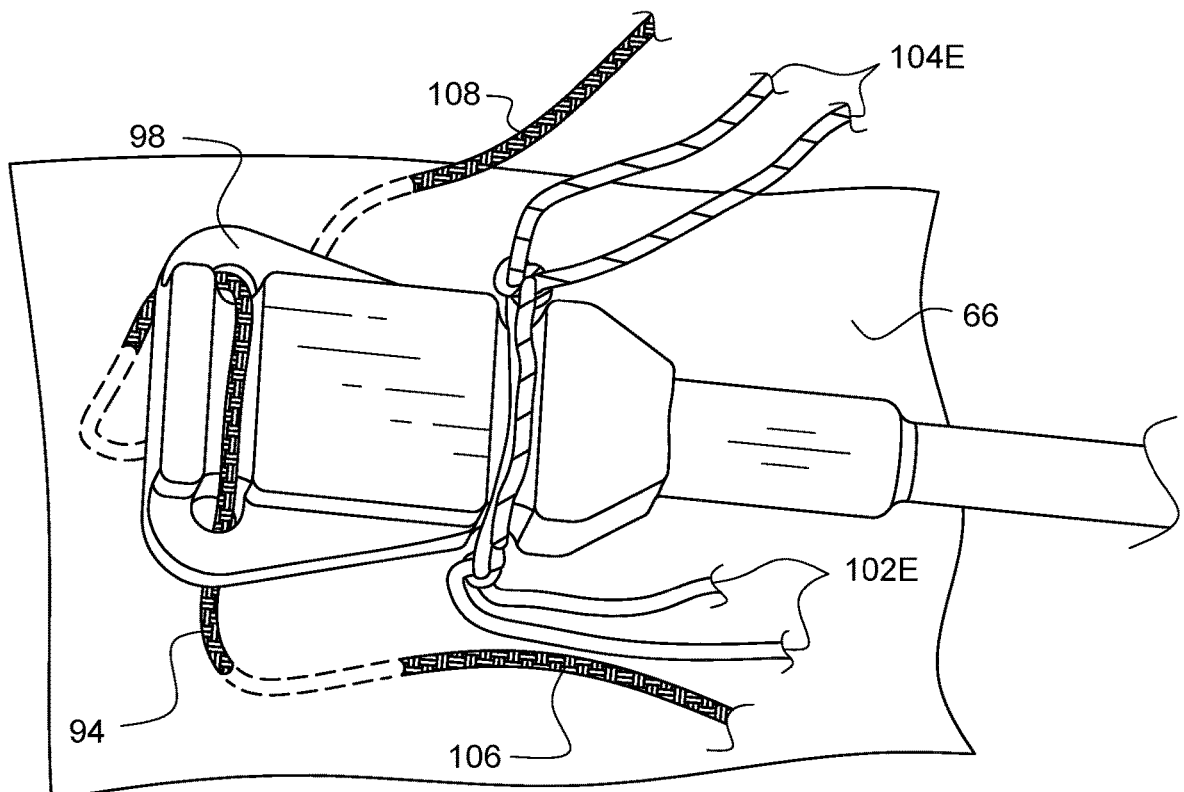
FIG. 8B illustrates a top view of the embodied pediatric pacemaker lead end of FIG. 8A.

The lead end 98 may be routed through the pediatric lead cannula 78 along the anchor suture towards the heart 66. The lead electrode 100 should face the heart. As illustrated in FIG. 8B, a first end 106 of the anchor suture 94 is aligned with the suture ends 102E of the first coupling suture 102. Similarly, a second end 108 of the anchor suture 94 is aligned with the suture ends 104E of the second coupling suture 104.

Figure 8C:
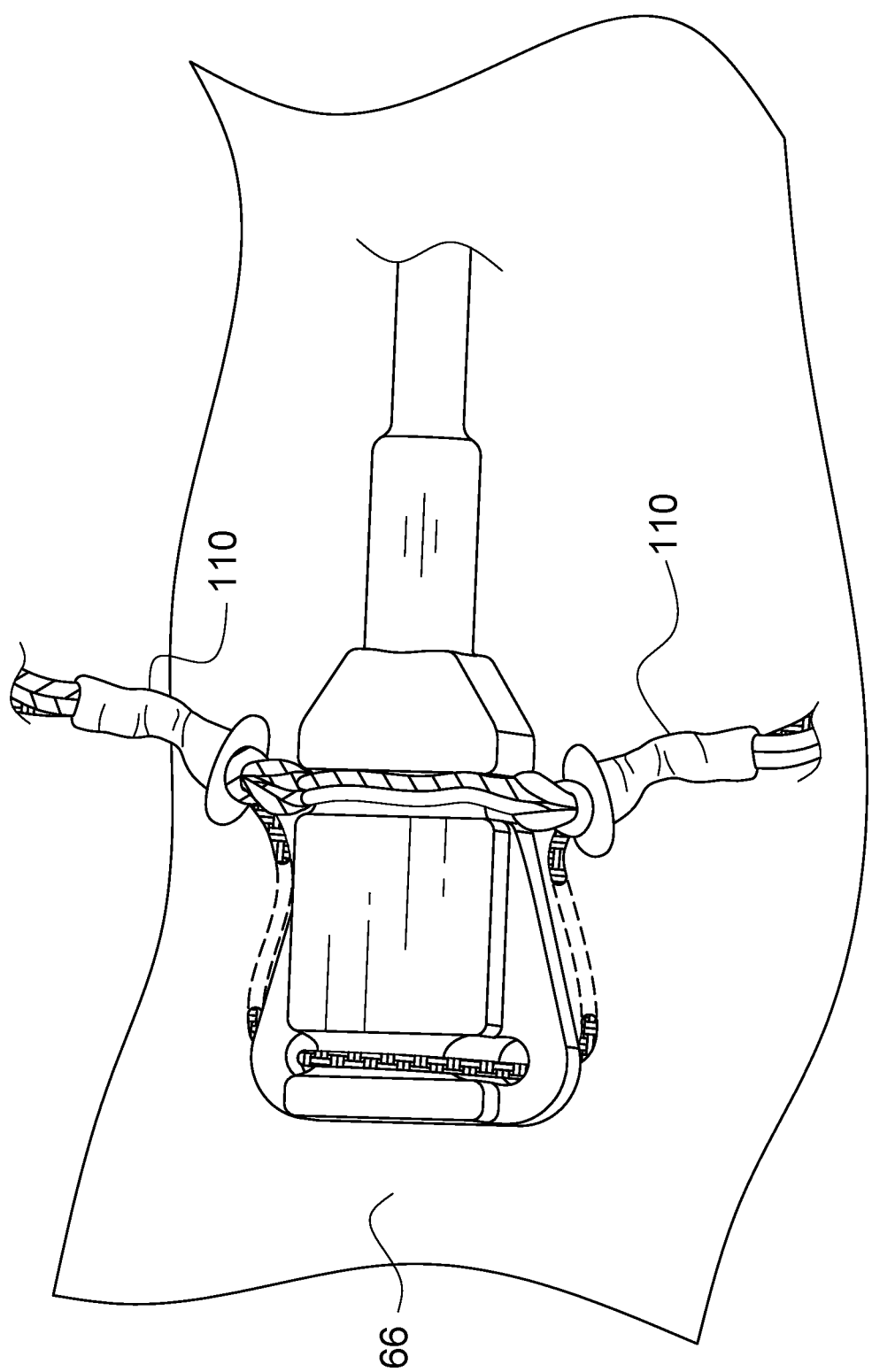
FIG. 8C illustrates the pacemaker lead end of FIGS. 8A and 8B secured to heart tissue with mechanical knots.

The first end 106 of the anchor suture 94 and the ends 102E of the first coupling suture 102 may be secured together against the side of the pacemaker lead end 98. Similarly, the second end 108 of the anchor suture 94 and the ends 104E of the second coupling suture 104 may be secured together against the other side of the pediatric lead 98. While handtied knots may be used, mechanical knots may be preferable. For example, FIG. 8C shows the pacemaker lead end 98 secured with the COR-KNOT® QUICK LOAD® mechanical knots 110 available from LSI Solutions, Inc. of Victor, N.Y. (See www.lsisolutions.com). Secure knots, in this case, mechanical knots 110, maintain the lead electrode 100 against the tissue of the heart.

Figure 8D:
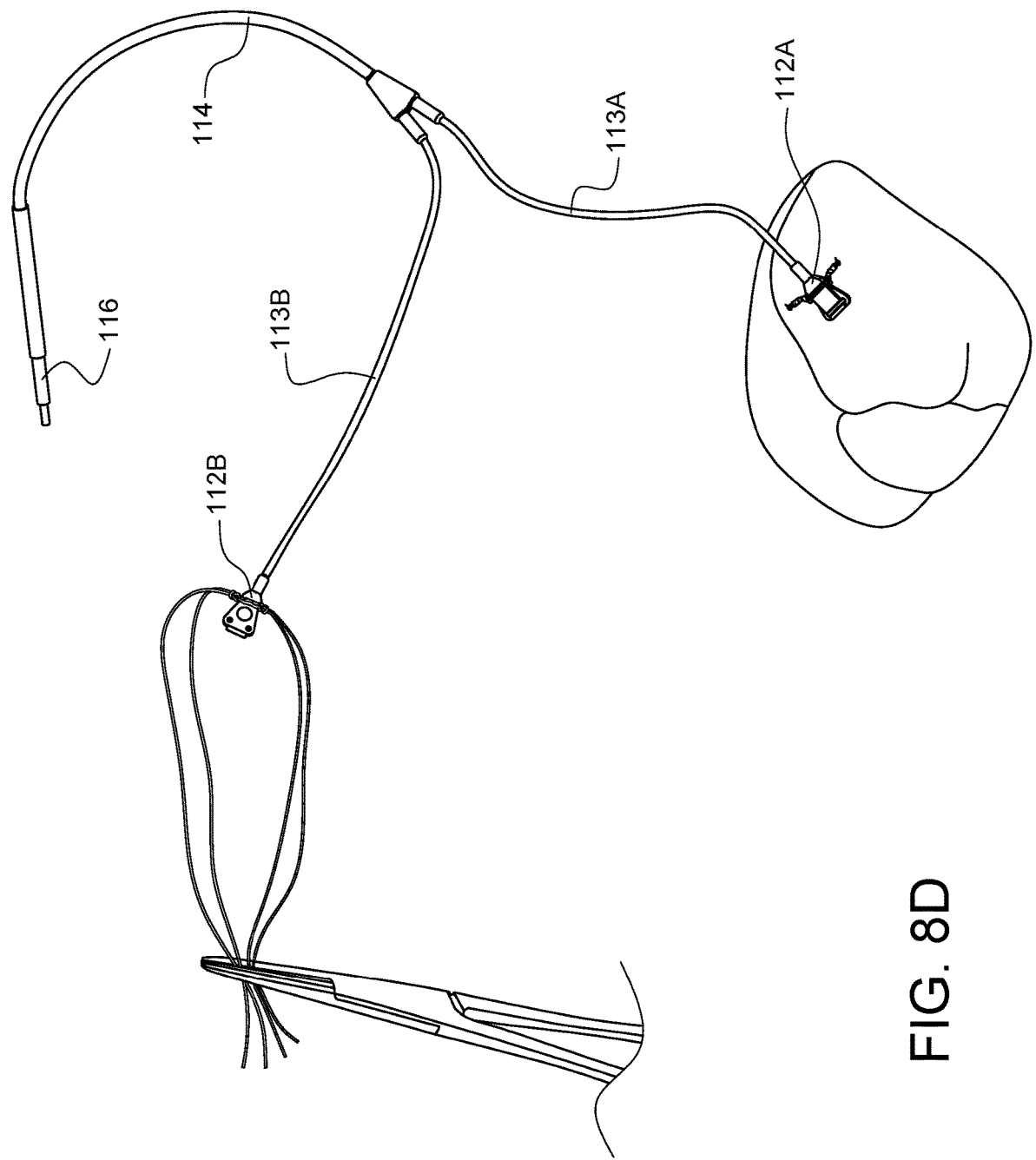
FIG. 8D illustrates an embodiment of a wiring casing having multiple pacemaker leads.

There will often be more than one pacemaker lead which will need to be attached to the heart. For example, like the pacemaker leads 112A, 112B shown in FIG. 8D, the first pacemaker lead 112A and the second pacemaker lead 112B may branch off from a single wiring casing 114 which has a connector 116 compatible with whichever pacemaker has been selected for the patient. This single wiring casing 114 branches into a first individual wiring casing 113A and a second individual wiring casing 113B, both terminating in the first pacemaker lead 112A and the second pacemaker lead 112B, respectively.

Figure 9A:
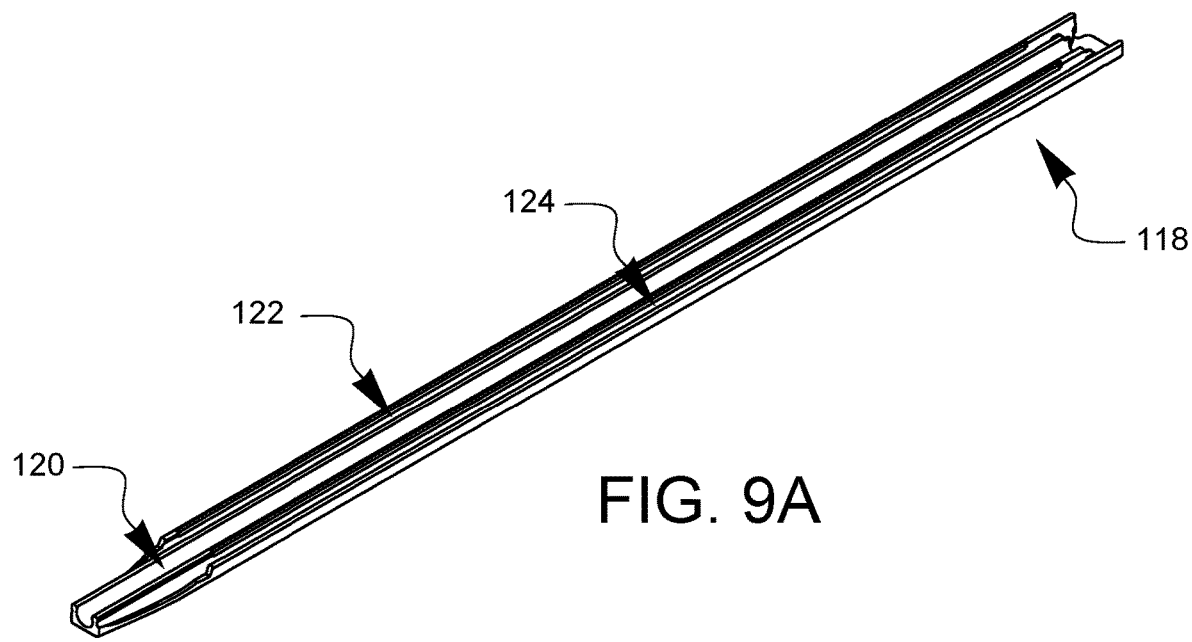
FIGS. 9A-9C show different perspective views of one embodiment of a lead brace.
Figure 9B:
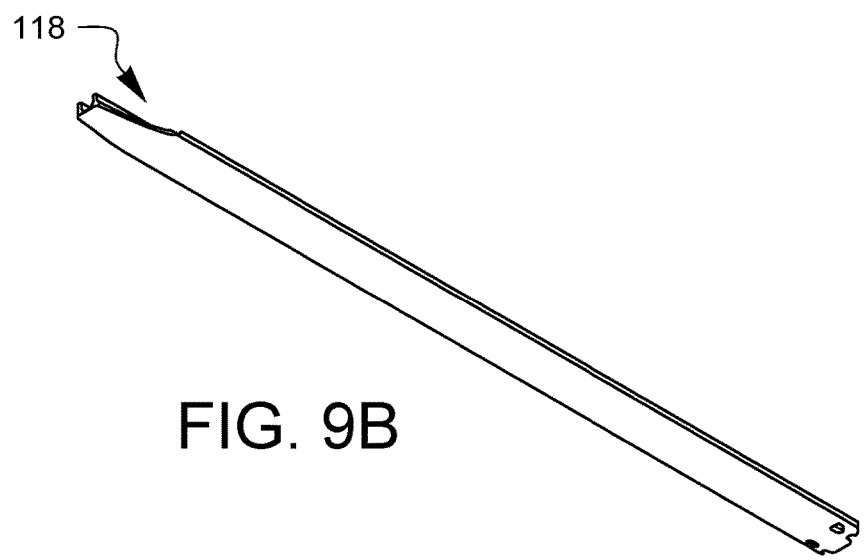
Figure 9C:

The pacemaker leads may be highly flexible, which can cause difficulties when trying to insert the leads through the patient's incision and access path through pericardium and into the space around the heart. One or more lead braces 118 may be provided to support the pacemaker lead 112A, 112B while it is being brought into position near the heart. One embodiment of a lead brace 118 is illustrated below in the top and bottom perspective views of FIGS. 9A and 9B, as well as in the top view of FIG. 9C.

The lead brace 118 has a center channel 120 which is sized to removably hold and support the pediatric lead 112A or 112B. Adjacent to the center channel 120 are two outside channels 122, 124. For purposes of suture management, the ends of the first coupling suture 102E attached to the lead end 98 are preferably threaded through a first coupling suture tube (to be shown later). One of the outside channels 122 is sized to removably hold and support the tube through which the ends 102E of the first coupling suture 102 run. Similarly, the ends 104E of the second coupling suture 104 attached to the lead end 98 are preferably threaded through a second coupling suture tube (to be shown later). The other outside channel 124 is sized to removably hold and support the tube through which the ends 104E of the second coupling suture 104 run. The lead brace 118 can help to overcome any tissue resistance when delivering the lead end 98 to the heart, and then the lead brace 118 can be removed. The lead brace 118 is also preferably sized to fit within the pediatric lead cannula 78.

As an alternative to delivering the lead end 98 to the heart after the horizontal mattress suture stitch has been placed, a minimally invasive surgical suturing device 126 may be provided which not only places the necessary anchor stitch 90 but also simultaneously introduces the lead end 98 to the space around the heart. The distal end of such a device 126 is shown in FIG. 10A.

A lead end rest 128 may be formed on the distal end of the suturing device 126. The ends 130 of the anchor suture 94 pass down into the suture device 126, while the middle loop 132 of the anchor suture 94 is kept organized in an anchor tube 134 that removably snaps into an anchor tube guide 136 on the back of the suturing device tip. Suture management tubes 138, 140 (which may also be referred to as coupling tubes 138, 140) are also provided for the ends of the first coupling suture 102 and the ends of the second coupling suture 104 as discussed above. A first individual wiring casing 129 attached to the lead end 98 is also kept organized along the distal end of the device 126 by being removably snapped into a tube support 146 (not shown in this view, but will be discussed later). The distal end of the suturing device 126 may be inserted through the pediatric lead cannula 78, and a tissue bite area 142 of the suturing device 126 may be positioned against the heart at a desired location for lead placement. The suturing operation of a suturing device to stitch a suture through the heart tissue in the tissue bite area 142 is known to those skilled in the art, while the features of the improved suturing device 126 pertaining to the lead, the configurations of anchoring suture and coupling sutures on the lead, suture management tubes, anchor tube, lead end rest, knotting to secure the pacemaker lead end, and their equivalents are not taught or suggested by the prior art. For example, see U.S. Patent Application Publication No. 2016/0345959 entitled "SUTURING DEVICE FOR MINIMALLY INVASIVE SURGERY AND NEEDLES AND METHODS THEREOF", the specification of which is hereby incorporated by reference in its entirety. Once the anchor suture mattress stitch has been placed in the heart tissue (for example, by using a curved needle which passes through tissue in the tissue bite area 142), the anchor tube 134 can be removed from the anchor tube guide 136 and the suturing device 126. The tubes 138, 140 holding the coupling suture 102, 104 ends may be held in position to help hold the lead end 98 near the anchor stitch and the device tip may be withdrawn from the patient. The device tip is designed to pull the ends of the anchor sutures out with it, so the surgeon is left with two anchor suture ends (which may be removed from the suturing device) and two tubes 138, 140, each tube holding the ends of a different coupling suture 102, 104. The first coupling tube 138 may be removed and the first coupling suture 102 may be secured with the first end 106 of the anchor suture 94 against the lead end 98 while it is properly oriented against the heart tissue. The second coupling tube 140 may also be removed and the second coupling suture 104 may be secured with the second end 108 of the anchor suture 94 against the lead end 98 to complete attachment of the lead end 98 to the heart. The resultant attachment will look like that of FIG. 8C.

Figure 10A:
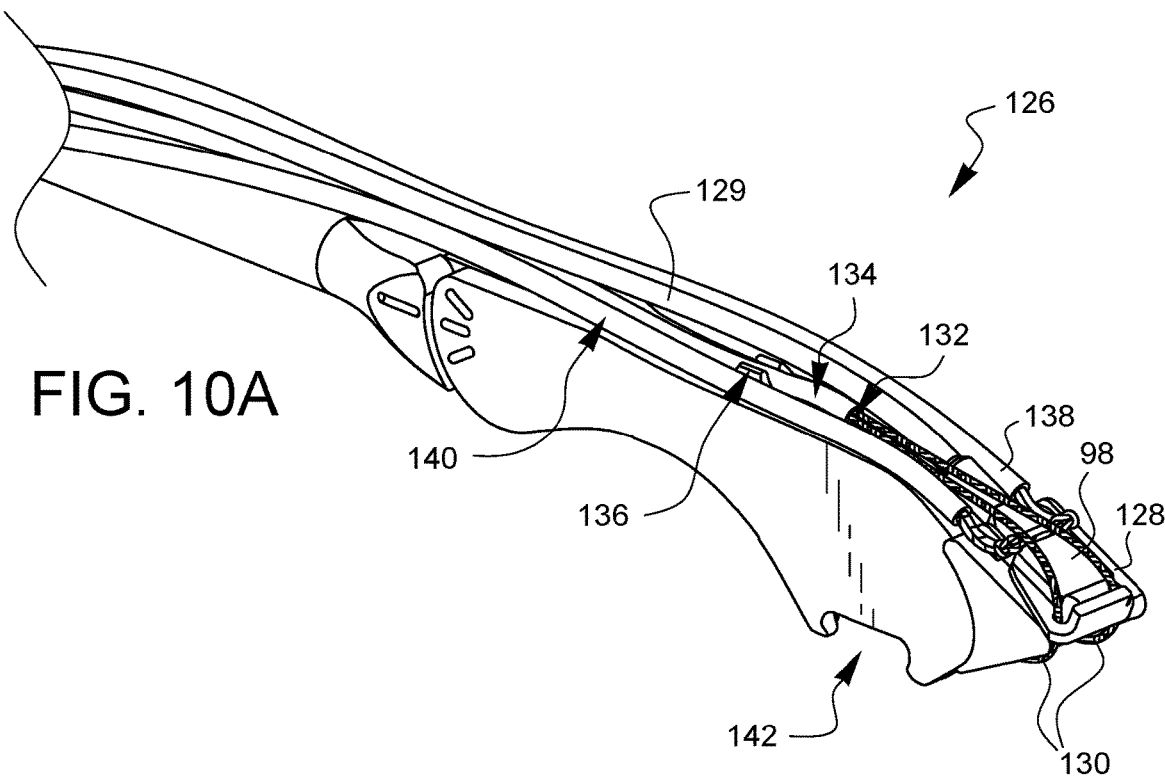
FIG. 10A illustrates the distal end of one embodiment of a minimally invasive surgical suturing device for placing an anchor stitch for a pacemaker lead and delivering the pacemaker lead end to the space around the heart.
Figure 10B:
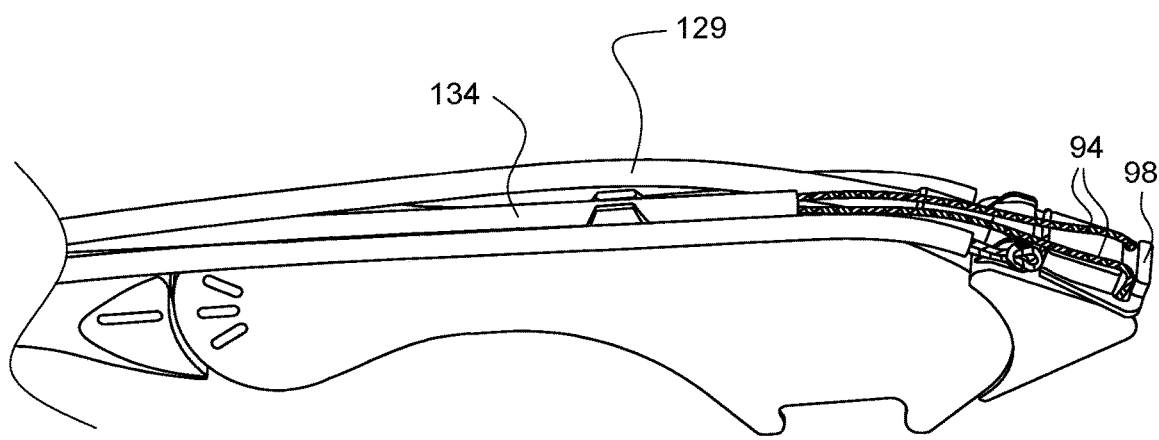
FIGS. 10B-10D illustrate the distal end of the minimally invasive surgical suturing device of FIG. 10A from a variety of different perspectives.
Figure 10C:
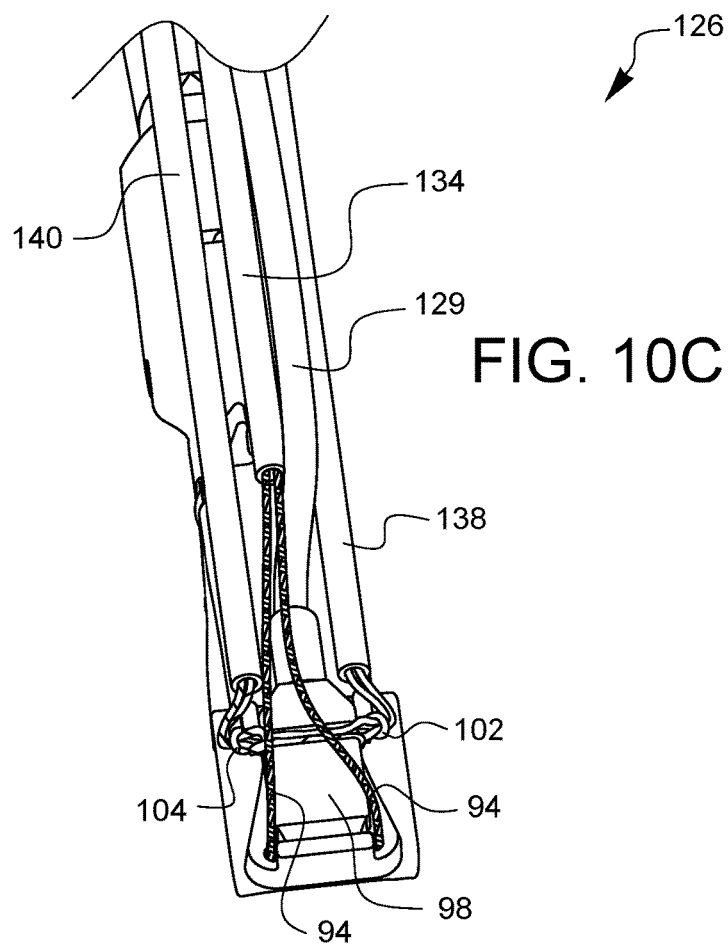
Figure 10D:
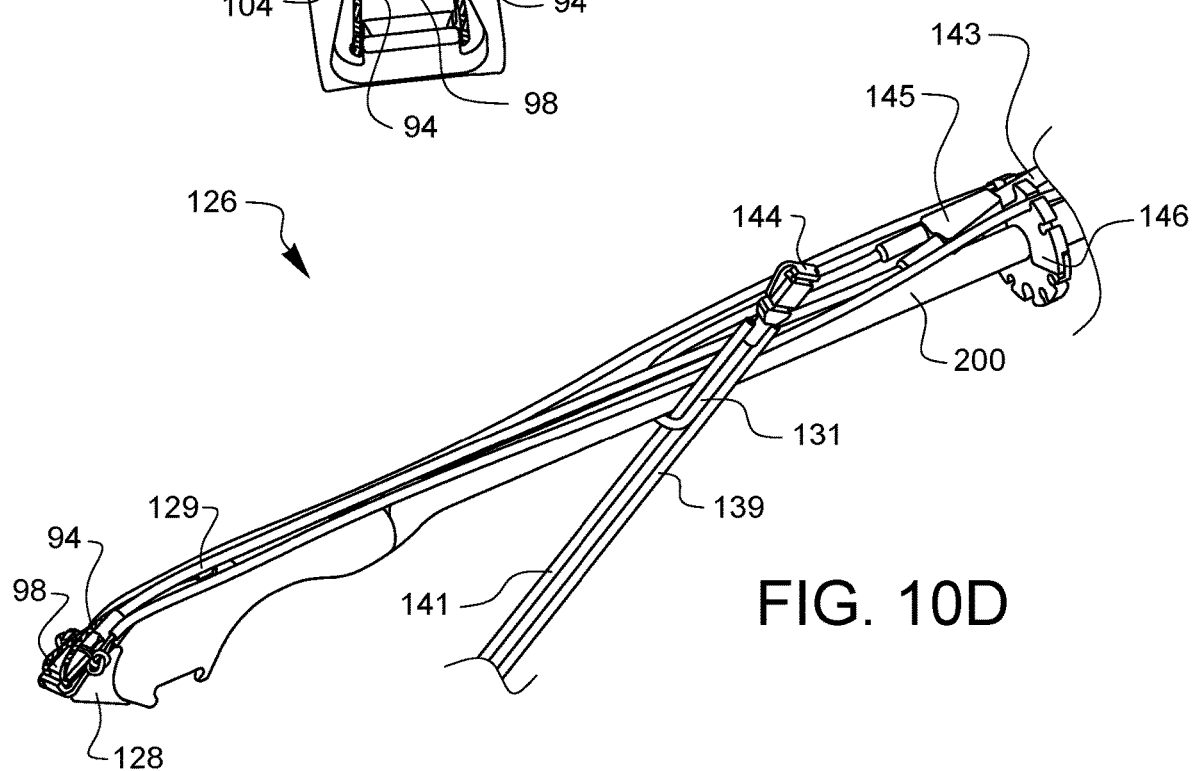

FIGS. 10B-10D show the distal end of the minimally invasive surgical suturing device from a variety of different perspectives.

FIG. 10D illustrates another perspective of the distal end of the minimally invasive surgical suturing device of FIG. 10A. This view includes the distal end of the device 126 as well as a tube support 146 at a proximal end of the shaft 200. This perspective also shows one way of managing more than the one pacemaker lead end 98 during a surgical procedure. The second pacemaker lead end 144 is prepared in a similar manner as described in regard to the first pacemaker lead end 98, and also has an anchor suture and anchor suture tube (not visible in this view). The second pacemaker lead end 144 having a second individual wiring casing 131 is also secured with a coupling suture (not visible in this view) constrained on either side of the second pacemaker lead end 144 and second individual wiring casing 131 within a first coupling suture tube 139 and a second coupling suture tube 141. While the first lead end 98 is being attached to the surface of the heart as previously described, this second pacemaker lead end 144 can be wound around the shaft 200 of the suturing device 126 while the single wire casing 143 is releasably held within the tube support 146. While other means of organizing this second pacemaker lead end 144 may be used or known to those skilled in the art, the illustration in FIG. 10D shows one such arrangement.

It may be helpful to have a pediatric lead cannula 78 which can be inserted next to the pediatric scope port 50. One embodiment of the pediatric lead cannula 78 is shown in the top and bottom perspective views of FIGS. 11A and 11B as well as in FIG. 11C. The pediatric lead cannula 78 has a handle 80 coupled to the proximal 82P end of a cannula portion 82. The proximal opening 84 of the cannula portion 82 is bounded on three sides, as is the distal opening 86 of the cannula. The main body 88 of the cannula portion 82 is bounded on four sides and is sized to provide clearance for a minimally invasive surgical suturing device to be passed through the cannula portion 82.

Figure 11A:
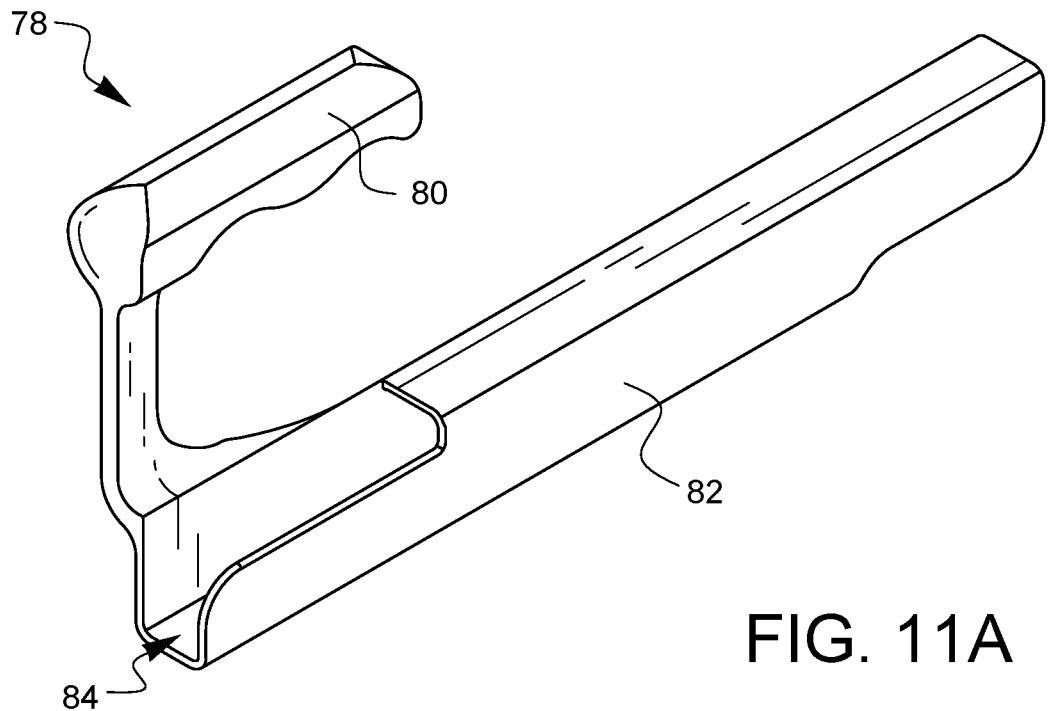
FIGS. 11A-11C show different views of one embodiment of a pediatric lead cannula.
Figure 11B:
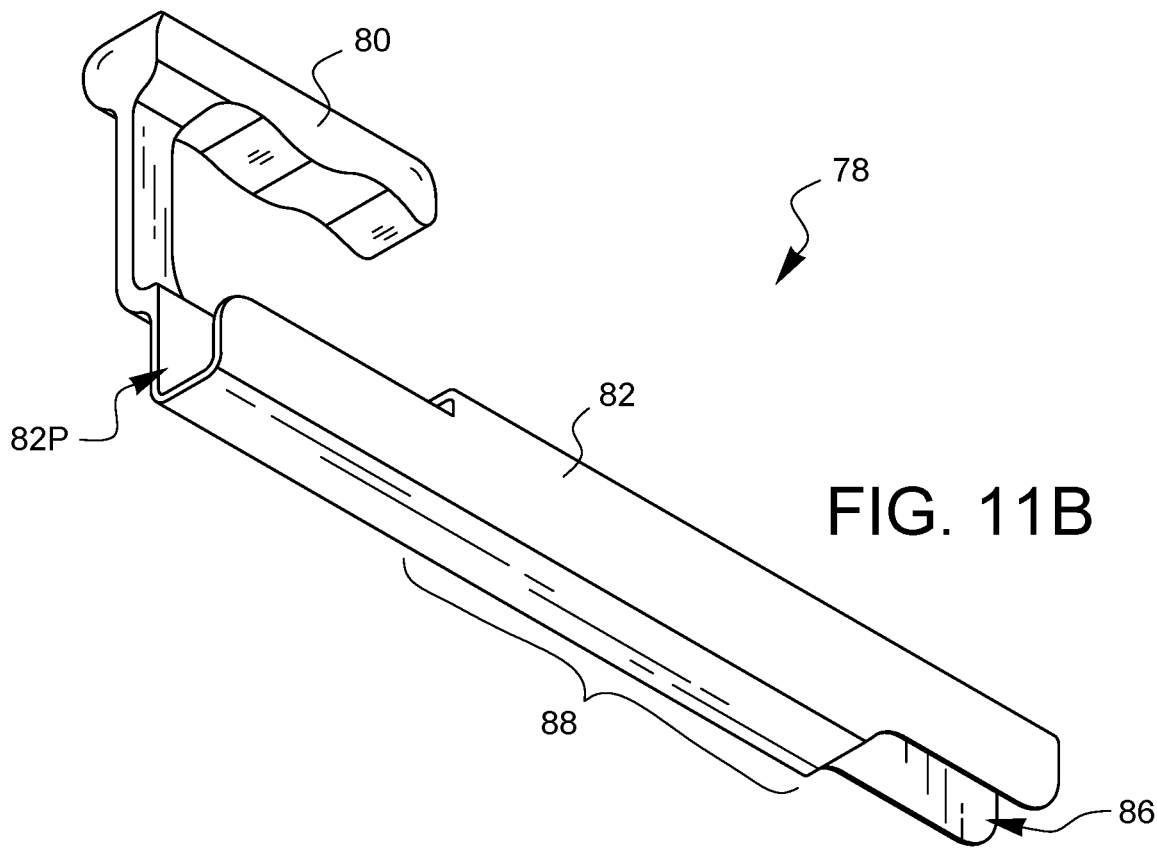
Figure 11C:
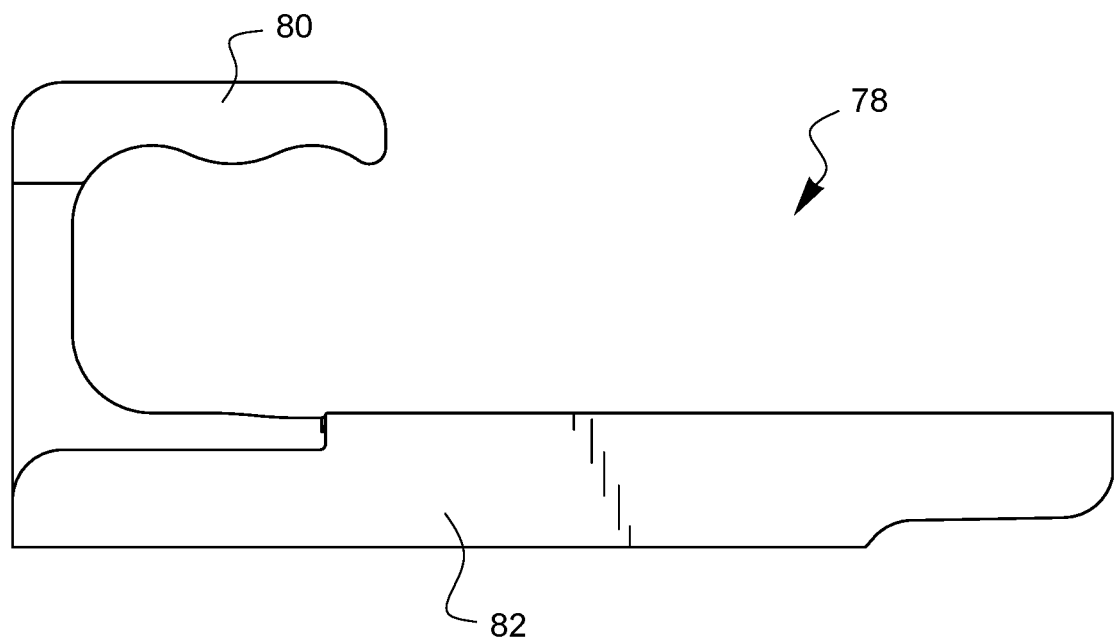
Figure 12E:
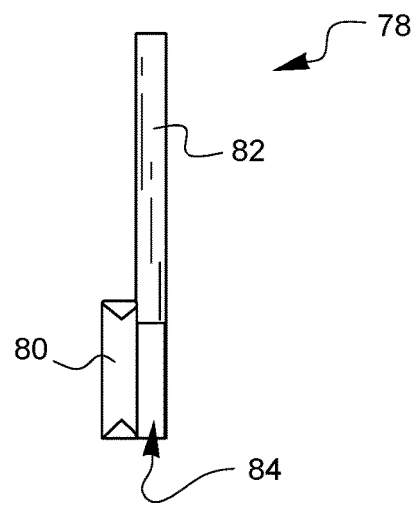
FIGS. 12A, 12B, 12C, 12D, 12E, 12F are front (proximal side), left, right, rear (distal side), top, and bottom elevation views, respectively, of the pediatric lead cannula of FIGS. 11A-11C.
Figures 12A, 12B, 12C, 12D:
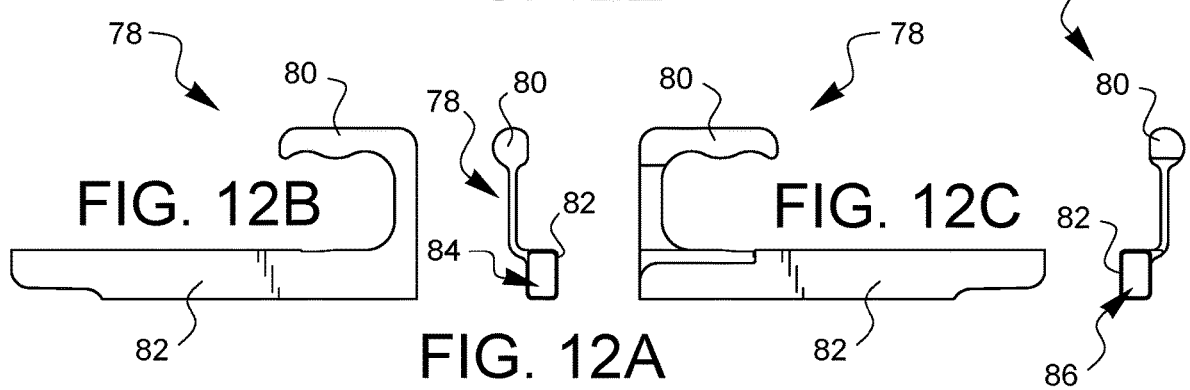
Figure 12F:
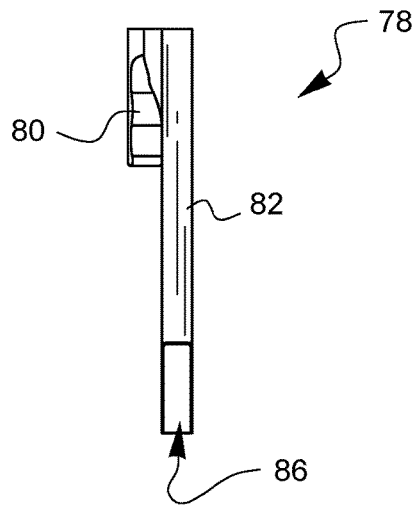

FIGS. 12A, 12B, 12C, 12D, 12E, 12F are front (proximal side), left, right, rear (distal side), top, and bottom elevation views, respectively, of the pediatric lead cannula 78 shown in FIGS. 11A-11C. Other means of providing clearance for minimally invasive surgical suturing devices to be passed through during the placement of a pediatric pacemaker lead may be used, such as cannulas having a main body having an alternate shape or configuration of open sides on the proximal or distal end of the cannula.

Figure 13A:
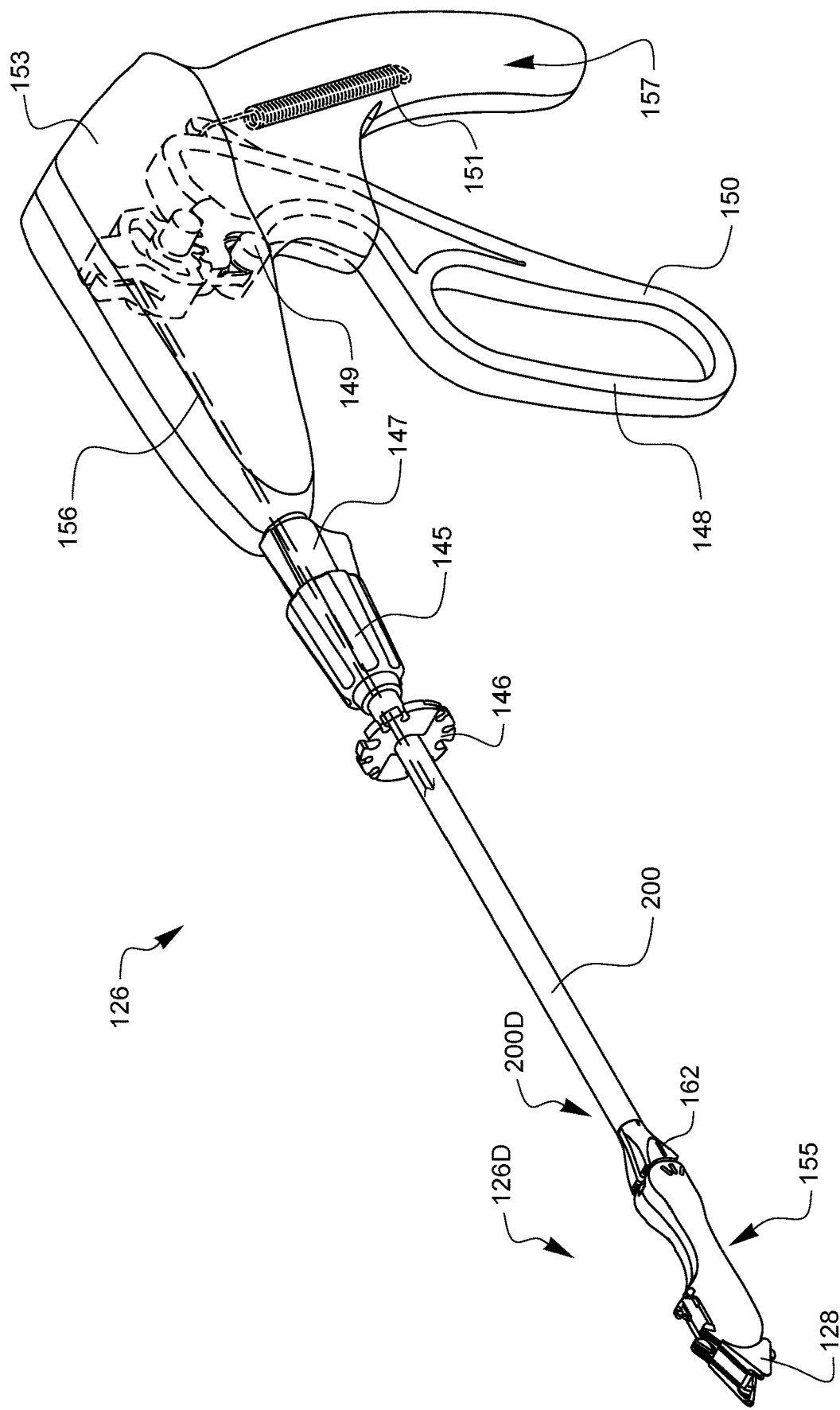
FIG. 13A is a perspective view of an embodiment of a minimally invasive surgical suturing device.

FIG. 13A is a perspective view of the surgical suturing device shown in FIG. 10A. The minimally invasive surgical suturing device 126 has a device tip 155 which is located at a distal end 126D of the surgical suturing device 126 at the distal end 200D of a shaft 200. The shaft also includes a rotation adapter 147 and an articulation knob 145 which are configured to rotate and pivot or articulate the distal end 126D of the surgical suturing device 126, respectively, to achieve a more appropriate positioning during a minimally invasive surgical procedure. The surgical suturing device 126 also has an actuator 148 which is coupled to an actuator rod 156. The actuator 148 has an actuator pivot point 149 supported by a housing 153. An actuator spring 151 is coupled between the actuator 148 and the housing 153 to bias the actuator 148 into a retracted position, such as the position shown in FIG. 13A. In this embodiment, a handle 150 of the actuator 148 is configured to be moved from the retracted position of FIG. 13A to an engaged position where the actuator 148 is pivoted around the pivot point 149 to move the handle 150 closer to a grip 157 of the housing 153. Since the pivot point 149 is between the handle 150 and the point where the actuator rod 156 couples to the actuator 148 in this embodiment, the actuator rod 156 will move distally, toward the device tip 155 when the handle 150 is squeezed towards the grip 157. Conversely, in this embodiment, the actuator rod 156 will move proximally, toward the housing 153, when the handle 150 is moved away from the grip 157. Although the actuator 148 in this embodiment includes a lever, other embodiments may utilize a variety of other actuators, including, but not limited to, a control knob, a control wheel, a solenoid, a slider, a screw, one or more gears, one or more pulleys, a motor, or any plurality and/or combination thereof. The assembly of this minimally invasive surgical suturing device 126 will be discussed in further detail with regard to FIGS. 13B-13F. While some features and components of a minimally invasive surgical suturing device used to stitch a suture through the heart tissue are known to those skilled in the art, features of the improved suturing device 126 pertaining to the lead, the configurations of anchoring suture and coupling sutures on the lead, suture management tubes, anchor tube, lead end rest, knotting to secure the pacemaker lead end, and their equivalents are not taught or suggested by the prior art. For example, see U.S. patent application Ser. No. 15/889,107, published as US20180221012A1, entitled "SUTURING DEVICE FOR MINIMALLY INVASIVE SURGERY", the specification of which is hereby incorporated by reference in its entirety.

Figure 13B:
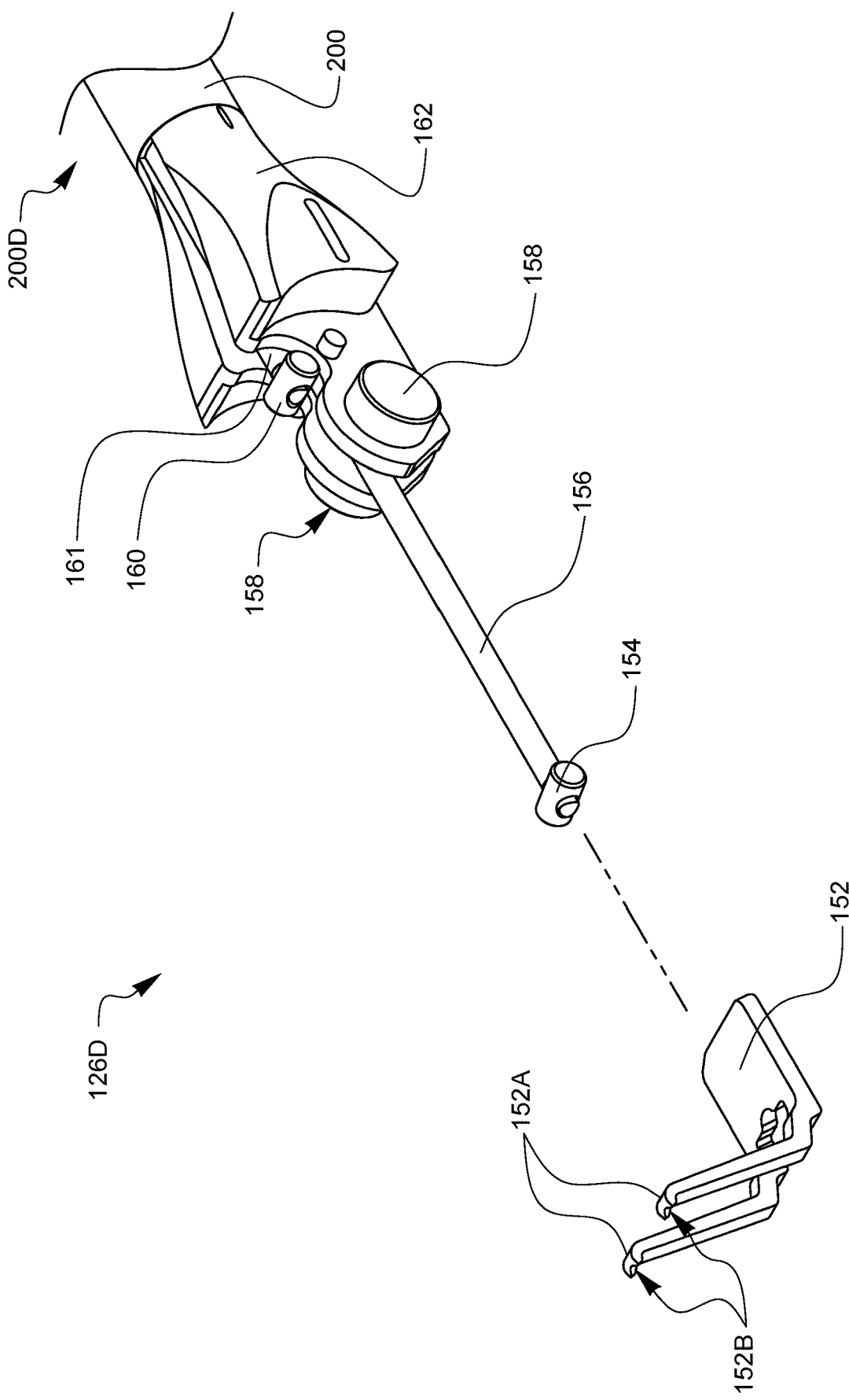

FIGS. 13B-13F are exploded views illustrating assembly of the distal end of the minimally invasive surgical suturing device of FIG. 13A. FIG. 13B is an exploded perspective view of part of the assembly of a distal end of the surgical suturing device shown and described in regard to FIG. 13A. At the distal end 200D of the shaft 200, an actuator rod 156 extends from a first pivotable arm 162 of the suturing device 126. The first pivotable arm 162 also has an axle 158 on either side. An actuator end effector 154 is attached to the end of the actuator rod 156. This actuator end effector 154 and actuator rod 156 are inserted between the arms 152A of a latch spring 152. The latch spring 152 also has a notch 152B at the end of each of the arms 152A.

Figure 13C:
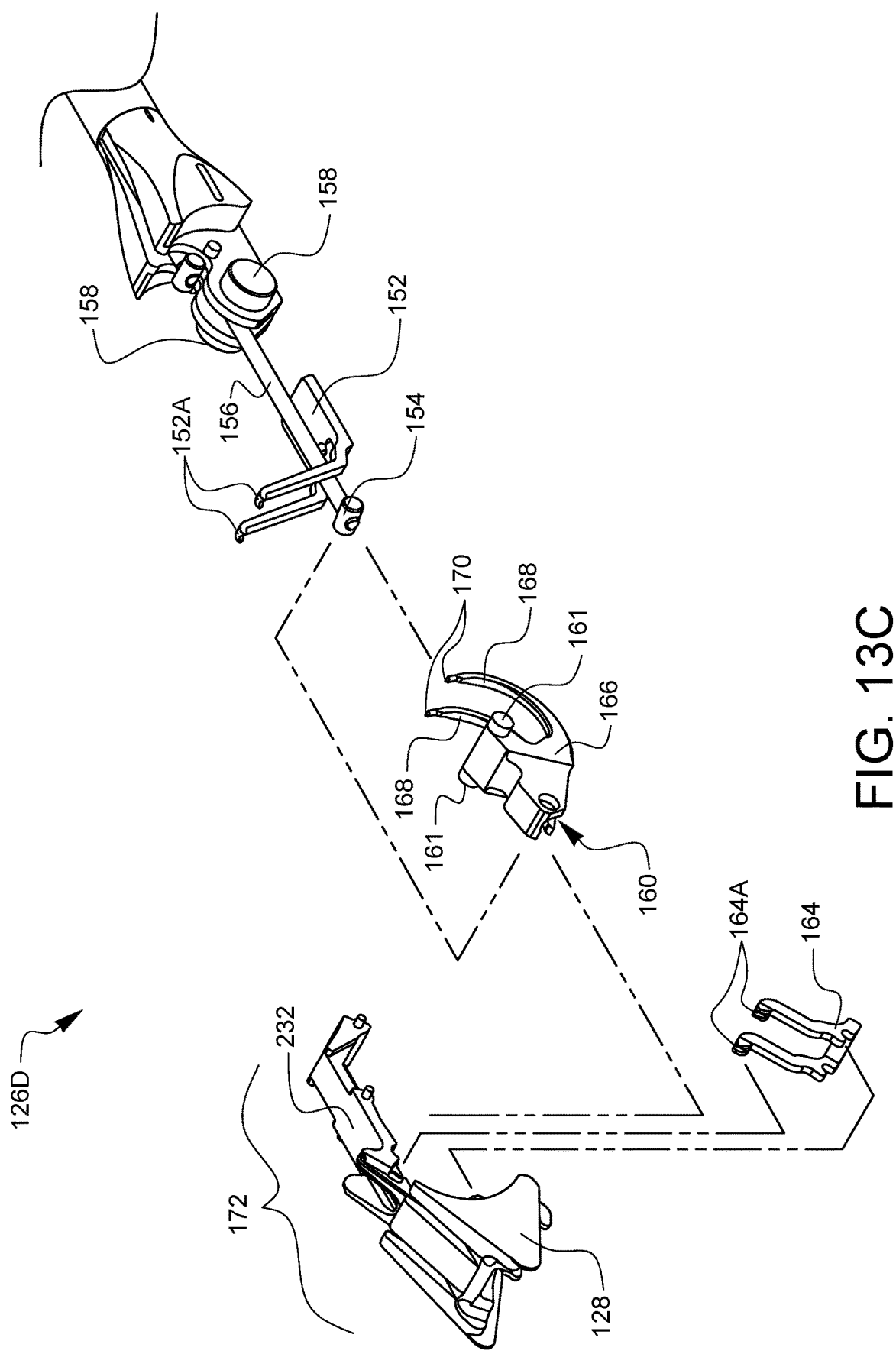

FIG. 13C is an exploded perspective view of part of the assembly of a distal end of the surgical suturing device of FIG. 13A. As described previously, the actuator rod 156 has an actuator end effector 154 coupled to a distal end of the actuator rod 156. The actuator end effector 154 is inserted into an actuator coupler 160 defined by a needle 166. The needle 166 further defines two needle pivot axles 161, two needle arms 168 and ferrule engaging tips 170 at the end of each of the needle arms 168. While the embodiment shown has 2 curved needle arms 168 on the needle 166, other embodiments may include different numbers of needles and may or may not have a curved shape such as the one shown herein. Once the actuator coupler 160 of the needle 166 is attached to the actuator end effector 154, a ferrule backstop 164 which defines two arms 164A is attached to a lead end rest assembly 172 having a housing mount portion 232 and a lead end rest 128. The housing mount portion 232 and lead end rest 128 will be discussed later. This combined subassembly of the ferrule backstop 164 and the lead end rest assembly 172 are subsequently placed over the needle 166 and prepared for the final assembly steps of the device tip 155 at the distal end 126D of the minimally invasive surgical suturing device 126.

Figure 13D:
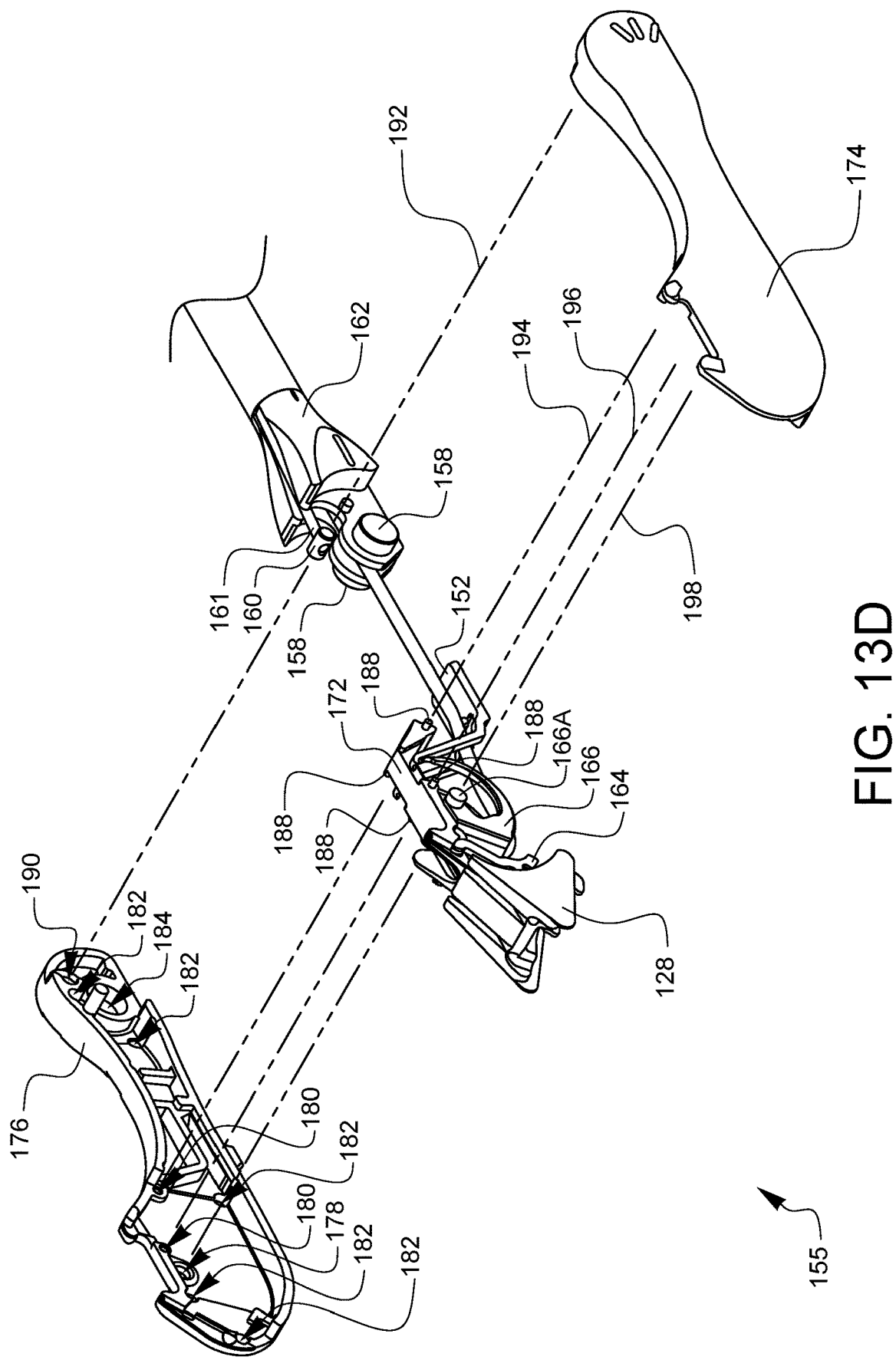

FIG. 13D is an exploded perspective view of a part of the assembly of the embodied surgical suturing device of FIG. 13A. The assembly of the device tip 155 of the minimally invasive suture device 126 is completed by enclosing the subassembly of FIG. 13C in two housing halves 174, 176. The housing halves 174, 176 each define two holes 180 that correspond to mounting pegs 188 on the lead end rest assembly 172. These mounting pegs 188 are inserted along longitudinal axis 194 and longitudinal axis 196. Housing half 176 further defines several holes 182 that correspond to pegs (not visible in this view) for the purpose of fixedly attaching the two housing halves 174, 176 together. A pivoting axle 166A on either side of curved needle 166 is inserted along longitudinal axis 198 and held within pivoting recess 178 on housing half 176 and a corresponding pivoting recess (not shown) in housing half 174. Axles 158 on the first pivotable arm 162 are fitted into recess 184 defined by the housing halves 176, 174. These housing halves 174, 176 are fixedly attached via friction fit, ultrasonic welding, adhesives or other means known to those skilled in the art while allowing the internal components to freely move. The exploded assembly of the embodiment in FIGS. 13A-D is just one of many possible assemblies, and it should be understood that those skilled in the art will realize other assembly configurations and methods of assembly which can produce the claimed surgical suturing device and its equivalents. Such assembly methods and their equivalents are intended to be included in the scope of this disclosure.

FIG. 13E is an exploded perspective view of a part of the assembly of the embodied surgical suturing device of FIG. 13A. The tube support 146 is assembled by combining a first tube support half 146A and a second tube support half 146B over the shaft 200 of the minimally invasive suture device 126. The tube support halves 146A, 146B each define several suture tube recesses 184 configured to releasably hold suture tubes, and a recess 186 configured to releasably hold single wire casings from pediatric leads. The two tube support halves 146A, 146B are placed over the shaft, interlocked together, and fixedly attached by a friction fit, adhesive, or by other suitable means of tube or lumen or wire organization are known to those skilled in the art.

Figure 13F:
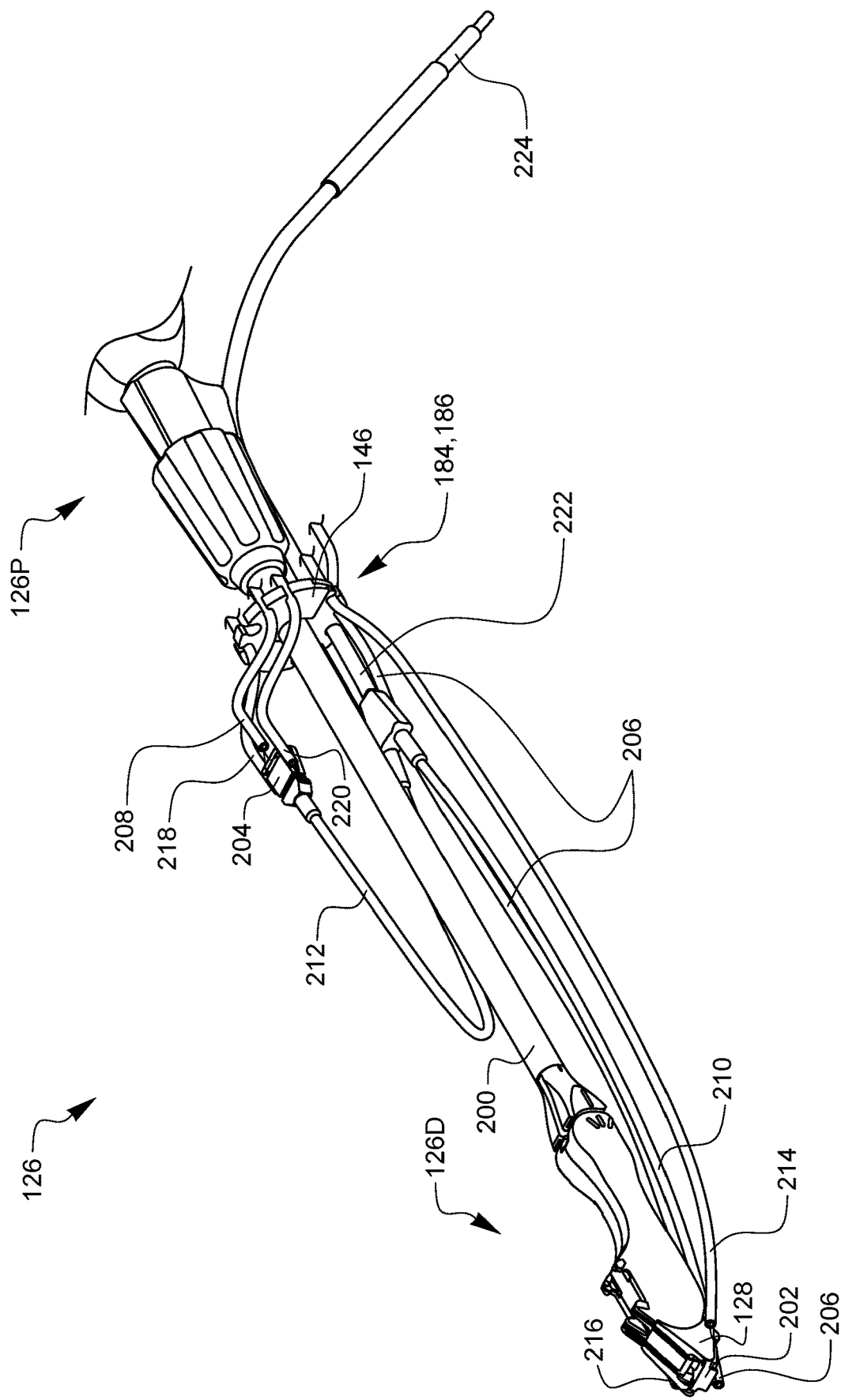
FIG. 13F is a perspective view of the distal end of the embodiment of the surgical suturing device of FIGS. 13A-13E.

FIG. 13F is an enlarged perspective view of the distal end of the embodied surgical suturing device of FIG. 13A, shown in an initial state of setup for a surgical procedure to attach a pacemaker lead end 202. Located at the distal end 126D of the minimally invasive suture device 126 is a first pacemaker lead end 202 releasably held in the lead end rest 128 of the minimally invasive suture device 126. The first pacemaker lead end 202 is a portion of a pediatric lead end assembly like the one illustrated in FIG. 8D. The first pacemaker lead end 202 has an anchor suture and two coupling sutures attached to the first pacemaker lead end 202 (not shown in this view) as described previously, which are organized by being constrained within a first anchor tube 206, first coupling suture management tube 214, and second coupling suture management tube 216, respectively.

Attached to the first pacemaker lead end 202 is a first individual wire casing 210. This first individual wire casing 210 and an anchor tube 206, a first coupling suture management tube 214, and a second coupling suture management tube 216 extend towards the proximal end 126P of the minimally invasive suture device 126. The anchor tube 206, first coupling suture management tube 214, and the second coupling suture management tube 216 are releasably held within the suture tube recesses 184 in the tube support 146, as previously described in regard to FIG. 13E. The first individual wire casing 210 merges into the single wire casing 222 which is releasably held in recess 186 in the tube support 146. This enables operation of the minimally invasive suture device 126 while keeping the anchor tube 206, first coupling suture management tube 214, second coupling suture management tube 216, first individual wire casing 210, and single wire casing 222 close to the shaft 200 of the minimally invasive suture device 126. As the first pacemaker lead end 202 is being attached to the heart, the second lead end 204 is held away from the distal end 126D of the minimally invasive suture device 126 and still close to the shaft 200 and kept free from interfering with the attachment procedure of the first pacemaker lead end 202. The second pacemaker lead end 204 also has an anchor suture and two coupling sutures attached to the second pacemaker lead end 204 as described previously which are organized by being constrained within a second anchor suture tube 208, first coupling suture management tube 218, and second coupling suture management tube 220, respectively. There is also a second individual wire casing 212 extending from the second lead end 204 which merges into the single wire casing 222. The second anchor suture tube 208, first coupling suture management tube 218, and second coupling suture management tube 220 are also releasably held within the suture tube recesses 184 in the tube support 146, as previously described, while convenient for suture and tube management during the attachment of the first pacemaker lead end 202. While this is one method of maintaining an organized set of pre-loaded sutures and suture tubes for a pediatric pacemaker lead attachment procedure, other effective methods of suture, suture tube, pacemaker lead, and pacemaker lead connection organization and management may be known and practiced by those skilled in the art. Such methods and their equivalents are intended to be included in the scope of this disclosure.

FIGS. 14A, 14B, 14C, 14D, 14E, 14F are front, left, right, rear, top, and bottom elevational views, respectively, of the lead end rest assembly of FIGS. 13B and 13C. The lead end rest assembly 178 defines a housing mount portion 232 and a lead end rest 128. The housing mount portion 232 further defines several mounting pegs 188 and a ferrule holder 238 on either side, corresponding to each of the curved needle arms and ferrule engaging tips, as described previously. The lead end rest 128 portion further defines two lead end guides 228 and an electrode recess 230 which are configured to releasably hold and receive a pacemaker lead end and pacemaker lead end electrode, respectively, during the placement of an anchor suture for the pacemaker onto the surface of a heart. The lead end rest 128 also defines two suture guides 226, which are configured to align suture with the ferrule holders 238. The two suture guides 226 define a center channel 236 in the lead end rest 128. Other means or similar features for retaining or aligning sutures may be used and would be known to those skilled in the art. Likewise, alternate sizes or shapes of the electrode recess 230 and lead end guides 228 could be used to accommodate various pacemaker lead ends, pacemaker leads, or other components of varying design.

Figure 15:
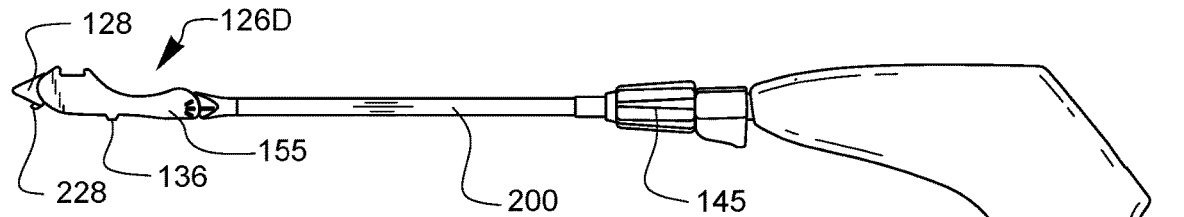
FIG. 15 is a side view of the entire minimally invasive surgical suturing device of FIG. 13A.

FIGS. 15-18 illustrate the surgical suturing device 126 from a variety of elevations and perspectives. FIG. 15 is a side view of the entire minimally invasive surgical suturing device of FIG. 13A. The distal end 126D of the minimally invasive surgical suturing device 126 has a lead end rest 128 as previously described in regard to FIGS. 13A-F and FIGS. 14A-F. On the underside of the lead end rest 128 are the end guides 228 and on the underside of the device tip 155 is the anchor tube guide 136. The proximal end 200P of the shaft 200 has an articulation knob 145 and the rotation adapter 147 as described previously. The surgical suturing device 126 also comprises a handle 150 and a lever 148 as described previously.

Figure 16:
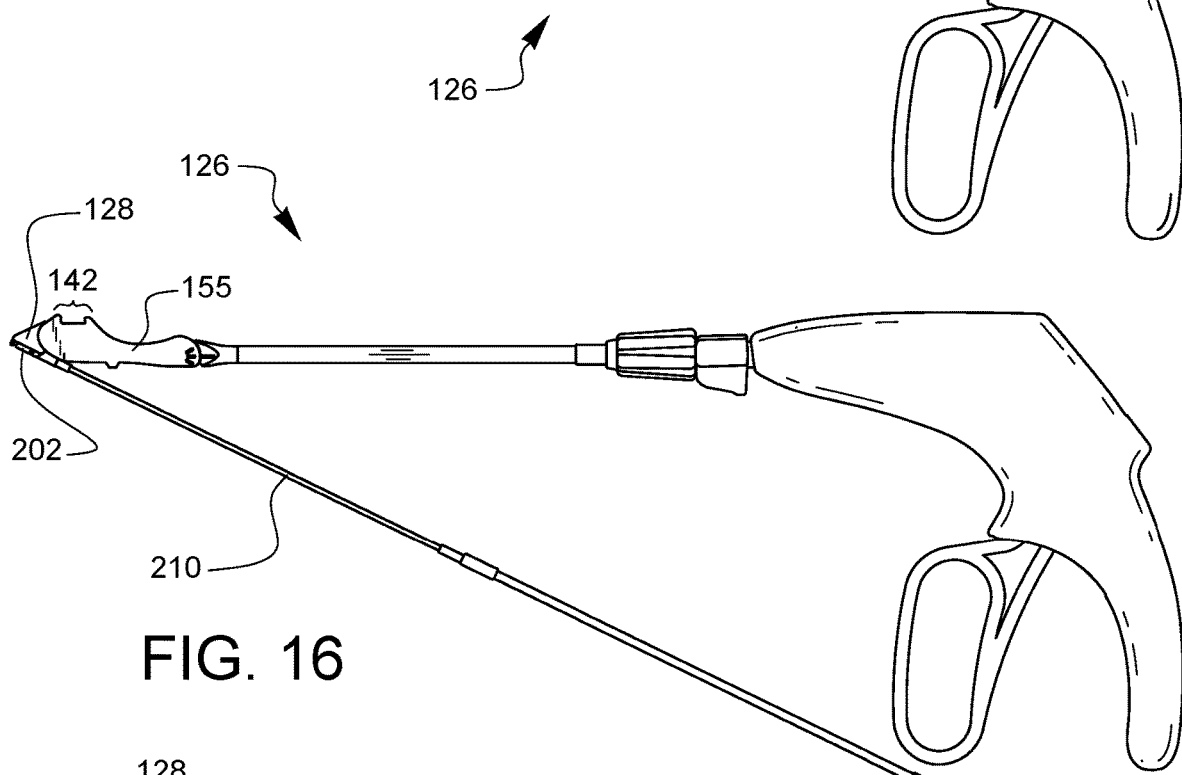
FIG. 16 is a side view of the minimally invasive surgical suturing device of FIG. 15 with a pediatric lead loaded into the lead end rest.

FIG. 16 is a side view of the minimally invasive surgical suturing device of FIG. 15 with a pediatric lead loaded into the lead end rest. FIG. 16 shows the distal end 126D of the minimally invasive surgical suturing device 126 with a pacemaker lead end 202 having a first individual wire casing 210 loaded and releasably held in the lead end rest 128 on the device tip 155.

Figure 17:
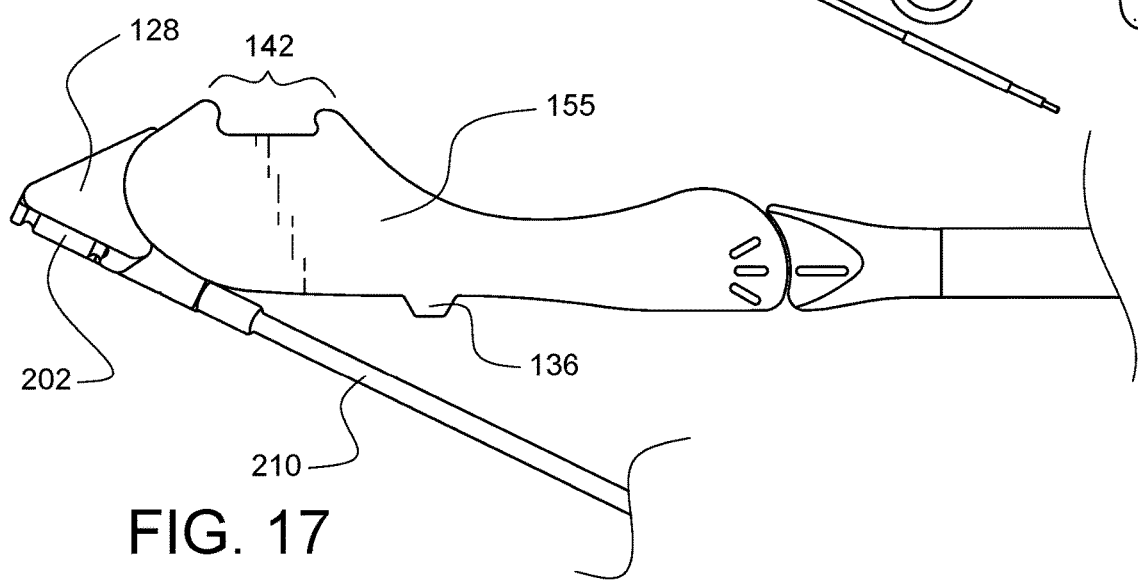
FIG. 17 is a side view of the distal end of the minimally invasive surgical suturing device of FIG. 15 with a pediatric lead loaded into the lead end rest.

FIG. 17 is a side view of the distal end of the minimally invasive surgical suturing device of FIG. 15 with a pediatric lead loaded into the lead end rest. On the underside of the device tip 155 is an anchor tube guide 136 opposite the tissue bite area 142, configured to receive the first individual wire casing 210 of the pacemaker lead end 202 configured to better organize the first individual wire casing 210 during a minimally invasive surgical procedure.

Figure 18:
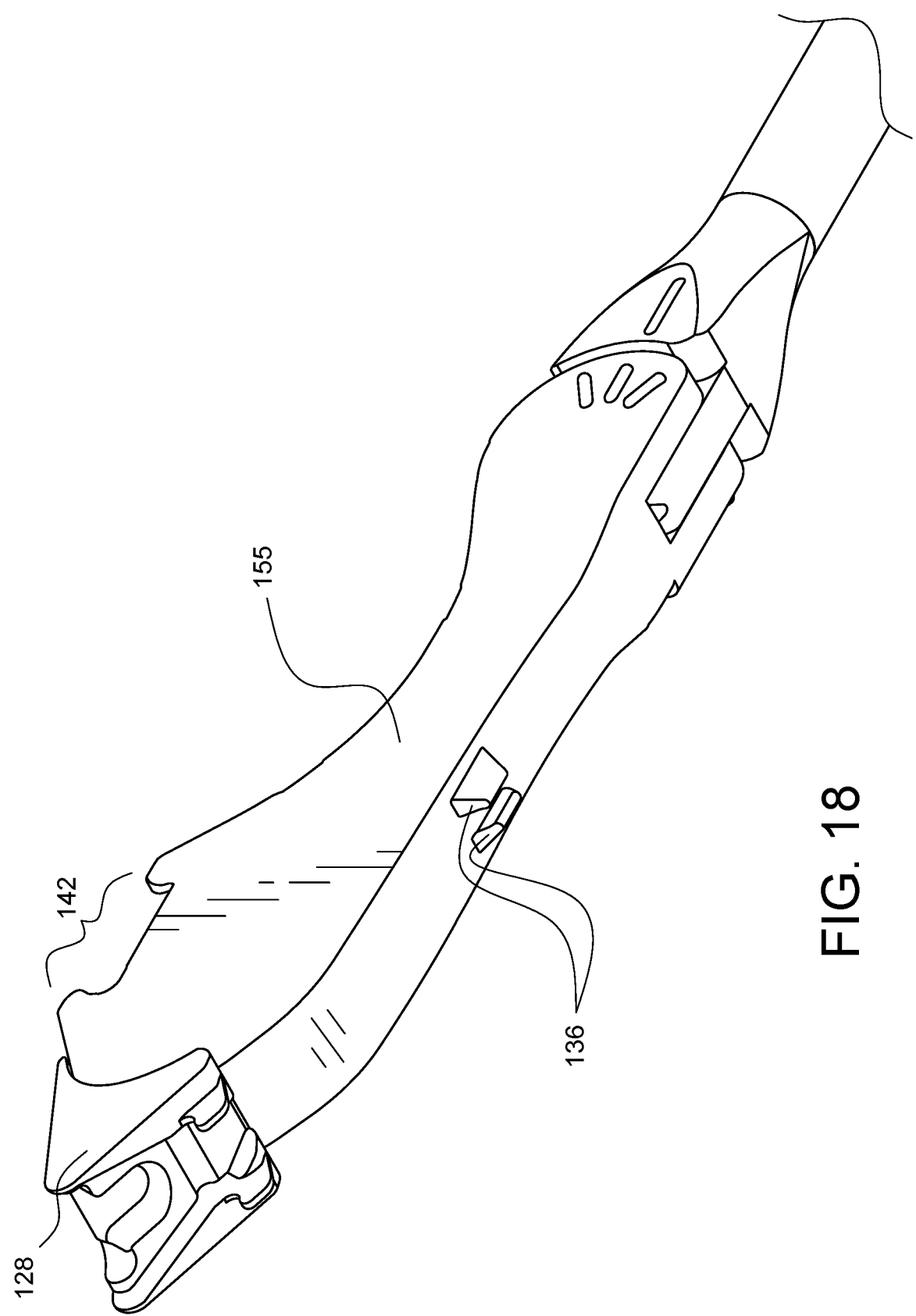
FIG. 18 is a bottom-left perspective view of the distal end of the minimally invasive surgical suturing device of FIG. 15.

FIG. 18 is a bottom-left perspective view of the distal end of the minimally invasive surgical suturing device of FIG. 15. FIG. 18 shows the underside of the device tip 155 with a view of the bottom side of the lead end rest 128 with the anchor tube guide 136.

Figure 19A:
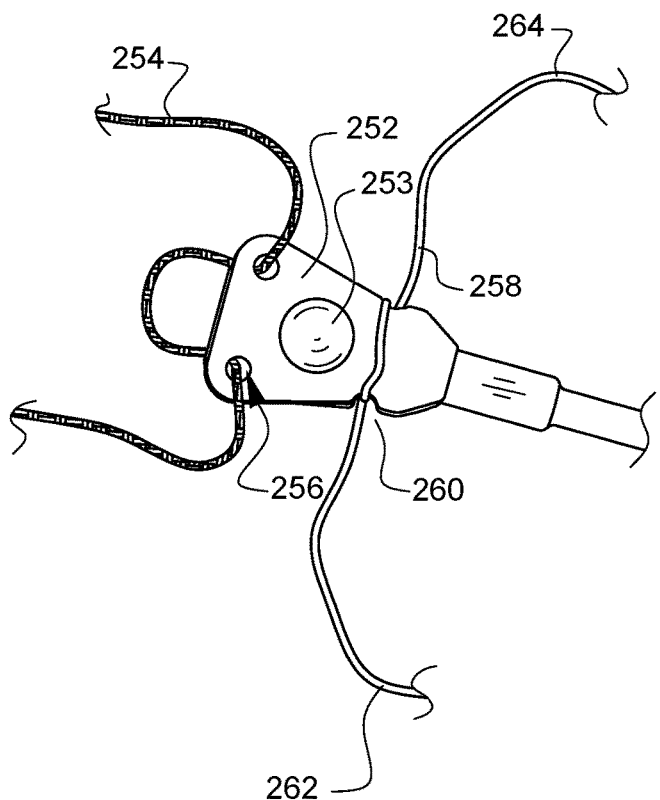
FIG. 19A illustrates a bottom view of one embodiment of a pediatric pacemaker lead end having an anchoring suture and a coupling suture.

FIG. 19A illustrates a bottom view of one embodiment of a pediatric pacemaker lead end having an anchoring suture and a coupling suture. The suture used to make this stitch in the heart may be called the anchor suture 254, and its ends should be routed as shown in FIG. 19A through anchor suture holes 256 in the pacemaker lead end 252. In this embodiment, the anchor suture holes 256 are located distally when compared to the lead electrode 253 on the pacemaker lead end 252. The lead electrode 253 is the portion of the pacemaker lead which will need to make good contact with the heart.

Figure 19B:
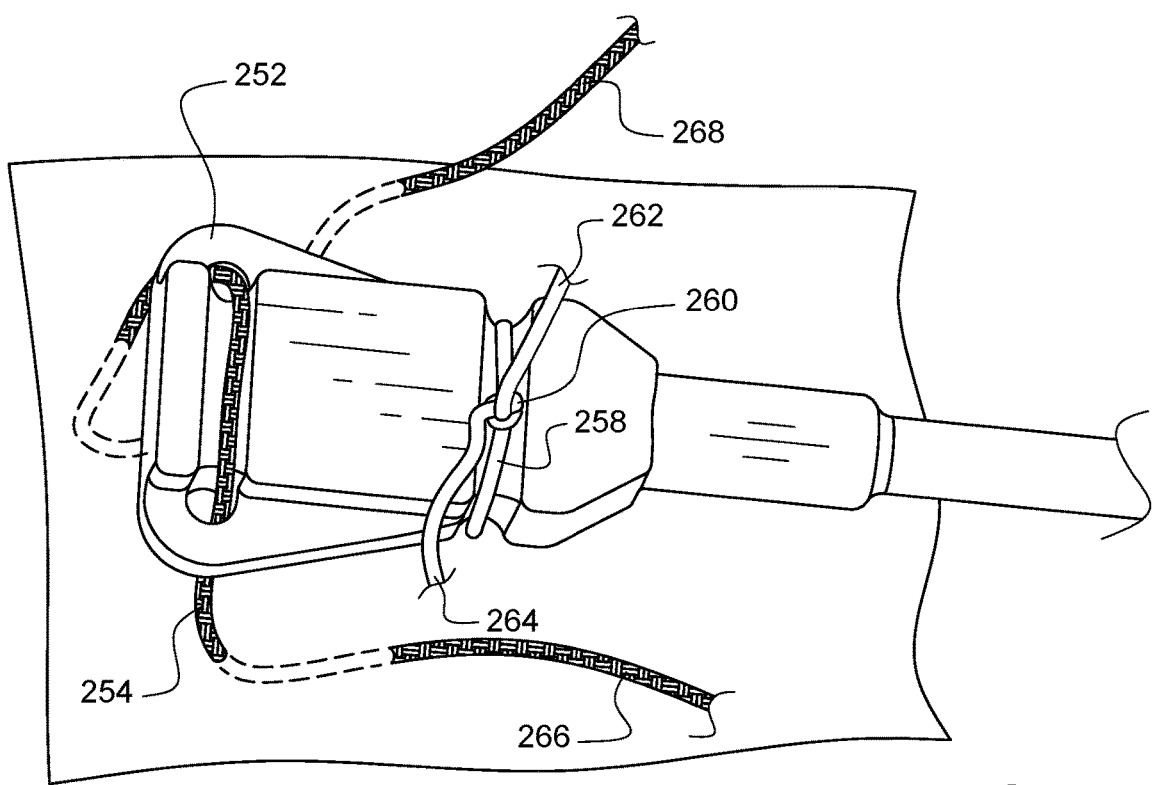
FIG. 19B illustrates a top view of the embodied pediatric pacemaker lead end of FIG. 23A.

As shown in FIG. 19A, a coupling suture 258 is coupled to the lead end 252 at a position proximal to the lead electrode 253 and held in place by a tied knot 260. In this embodiment, the coupling suture 258 has a first end 262 and a second end 264 and the first end 262 points in one direction while the second end 264 points in a substantially opposite direction. The lead end 252 may be routed through the pediatric lead cannula 78 along the anchor suture towards the heart 66. The lead electrode 253 should face the heart. FIG. 19B illustrates a top view of the embodied pediatric pacemaker lead end of FIG. 19A. As illustrated in FIG. 19B, a first end 266 of the anchor suture 254 is aligned with the first suture end 262 of the coupling suture 258. Similarly, a second end 268 of the anchor suture 254 is pointing in a substantially opposite direction when compared to the first end 266 of the anchor suture 254 and is aligned with the second end 264 of the coupling suture 258.

Figure 19C:
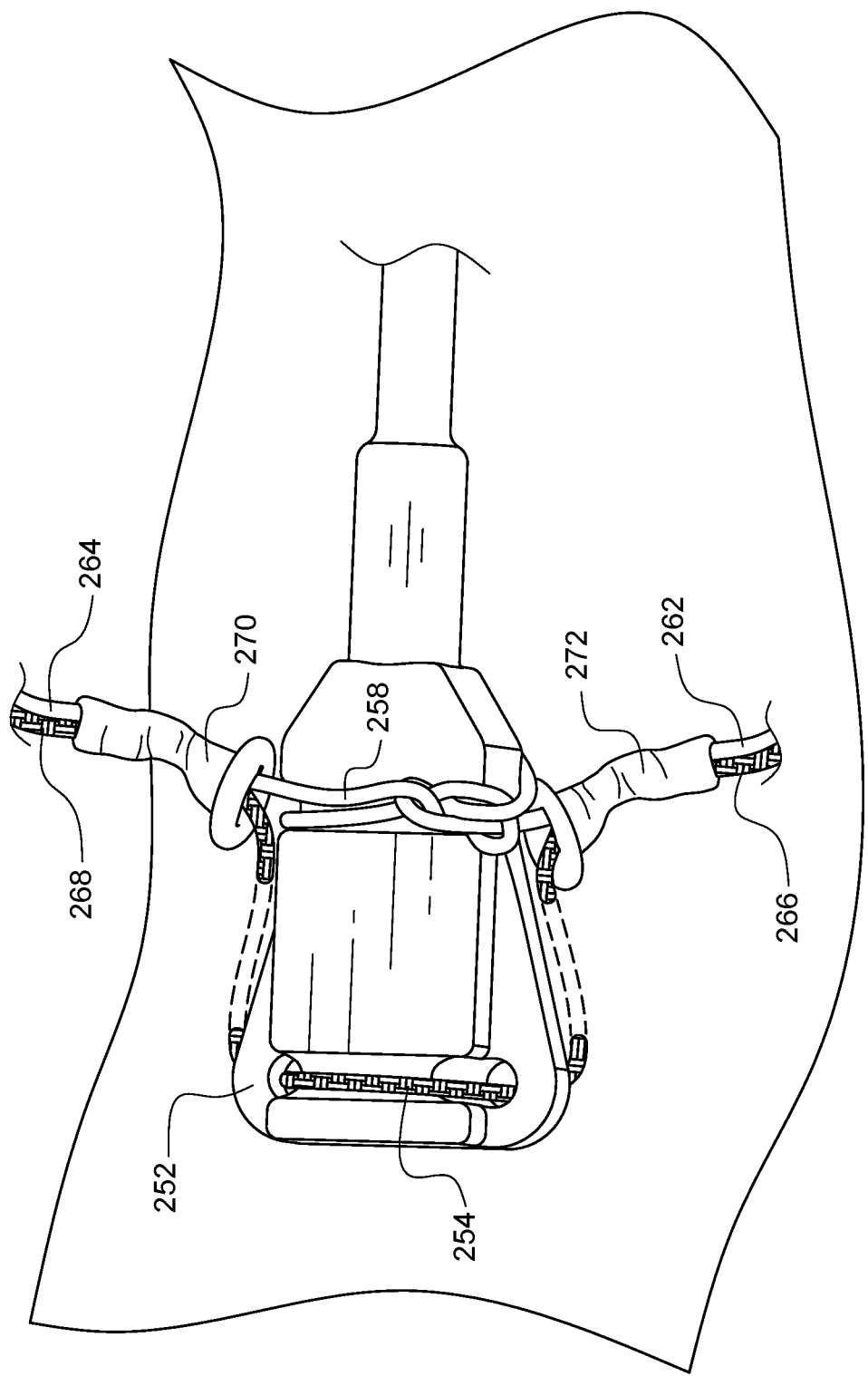
FIG. 19C illustrates the pacemaker lead end of FIGS. 19A and 19B secured to heart tissue with mechanical knots.

The first end 266 of the anchor suture 254 and the first end 262 of the coupling suture 258 may be secured together against the side of the pacemaker lead end 252. Similarly, the second end 268 of the anchor suture 254 and the second end 264 the coupling suture 258 may be secured together against the other side of the pediatric lead end 252. While handtied knots may be used, mechanical knots may be preferable. FIG. 19C illustrates the pacemaker lead end of FIGS. 19A and 19B secured to heart tissue with mechanical knots. For example, FIG. 19C shows the pacemaker lead end 252 secured with the COR-KNOT® QUICK LOAD® mechanical knots 270, 272 available from LSI Solutions, Inc. of Victor, N.Y. (See www.lsisolutions.com). Secure knots, in this case, mechanical knots 270, 272, maintain the lead electrode 253 against the tissue of the heart.

Figure 20A:
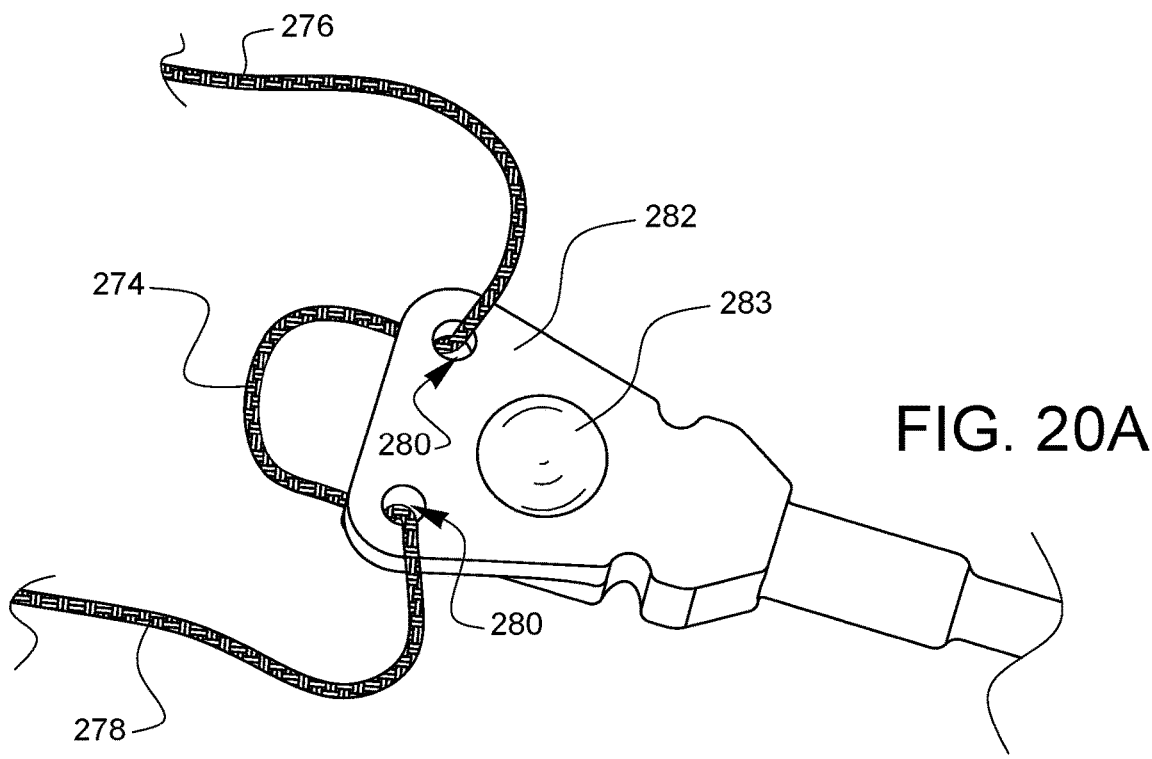
FIG. 20A illustrates a bottom view one embodiment of a pediatric pacemaker lead end having an anchoring suture.

FIG. 20A illustrates a bottom view one embodiment of a pediatric pacemaker lead end having an anchoring suture. The anchor suture 274 used to make this stitch in the heart and its ends should be routed as shown in FIG. 20A through anchor suture holes 280 in the pacemaker lead end 282. In this embodiment, the anchor suture holes 280 are located distally when compared to the lead electrode 283 on the pacemaker lead end 282. The lead electrode 283 is the portion of the pacemaker lead which will need to make good contact with the heart. The lead end 98 may be routed through the pediatric lead cannula 78 along the anchor suture towards the heart 66. The lead electrode 100 should face the heart.

Figure 20B:
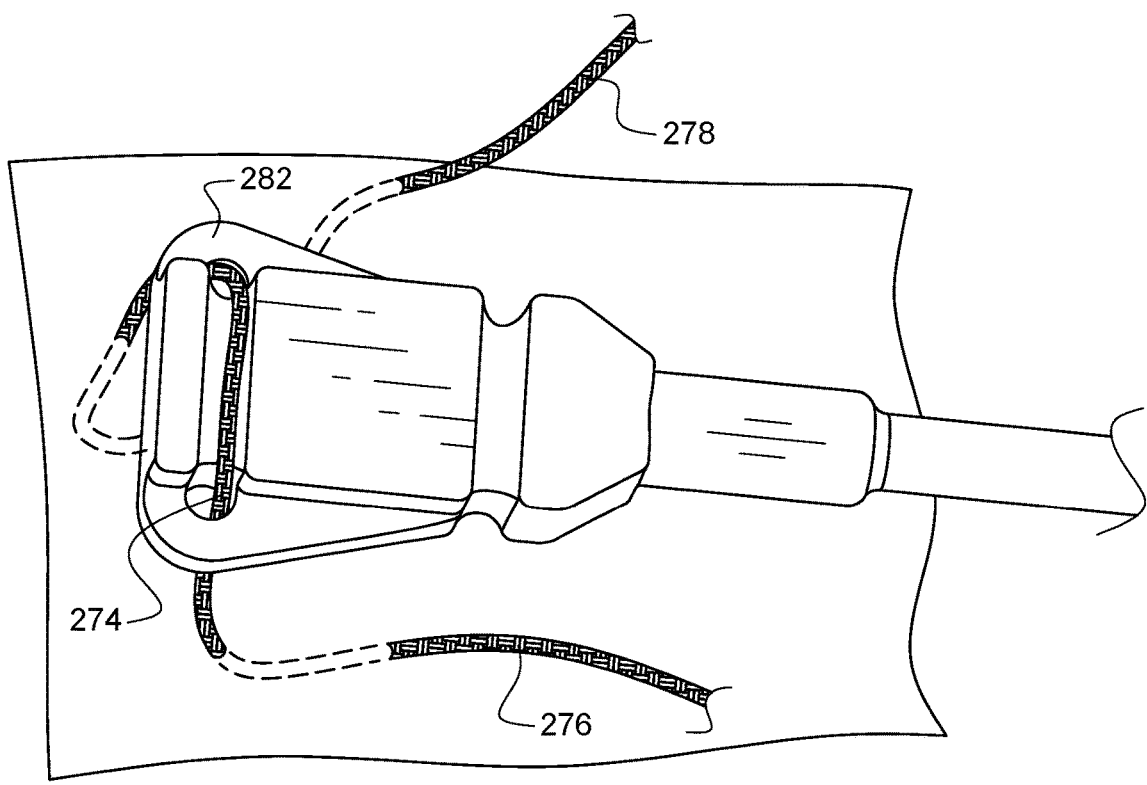
FIG. 20B illustrates a top view of the embodied pediatric pacemaker lead end of FIG. 24A.

FIG. 20B illustrates a top view of the embodied pediatric pacemaker lead end of FIG. 20A. As illustrated in FIG. 20B, a first end 276 of the anchor suture 274 and a second end 278 of the anchor suture 274 are shown exiting a horizontal mattress suture stitch on opposite sides of the pacemaker lead end 282.

Figure 20C:
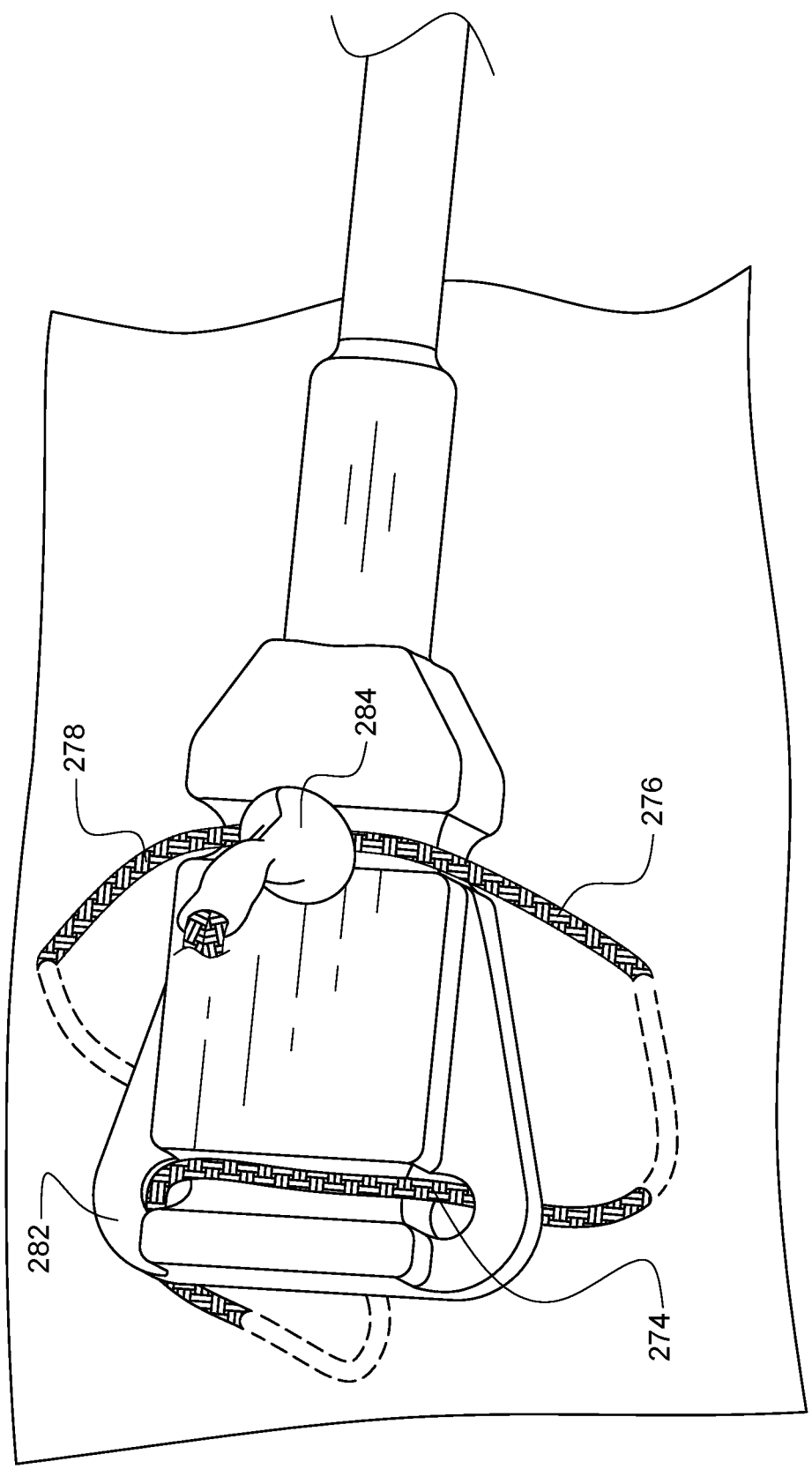
FIG. 20C illustrates the pacemaker lead end of FIGS. 20A and 20B secured to heart tissue with a mechanical knot.

The first end 276 of the anchor suture 274 and the second end 108 of the anchor suture 274 may be secured together against the side of the pacemaker lead end 282 opposite the side having the lead electrode 283. While handtied knots may be used, mechanical knots may be preferable. FIG. 20C illustrates the pacemaker lead end of FIGS. 20A, 20B secured to heart tissue with a mechanical knot. For example, FIG. 20C shows the pacemaker lead end 282 secured with the COR-KNOT® QUICK LOAD® mechanical knot 284 available from LSI Solutions, Inc. of Victor, N.Y. (See www.lsisolutions.com). A secure knot, in this case, a mechanical knot 284, maintains the lead electrode 283 against the tissue of the heart.

The embodiments discussed above have a wide variety of advantages over the prior art. They enable surgeons to place pacemaker leads in pediatric patients without the need for a sternotomy or thoracotomy, which will greatly reduce patient pain and recovery time. It should be understood that the concepts described herein are also applicable to non-pediatric patients. References made to pediatric leads should be interpreted as pacemaker leads which do not necessarily need to be for use in pediatric patients. The devices and methods disclosed herein, and their equivalents, make an endocardial approach unnecessary, thereby avoiding the downfalls of such procedures for lead placement. The minimally invasive tools enable surgeons to operate efficiently. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An assembly for pacemaker lead placement, comprising:
   a suturing device comprising:
      a shaft extending along a shaft axis from a proximal end to a distal end;
      a device tip extending from a proximal end to a distal end, wherein the proximal end of the device tip is disposed at or adjacent to the distal end of the shaft; and
      a first needle coupled to an actuator of the suturing device, the needle including a needle tip disposed at a distal end of the first needle, the actuator being displaceable between a first actuator position and a second actuator position such that when the actuator is displaced from the first actuator position to the second actuator position, the needle is displaced from a first needle position to a second needle position;
   a lead end rest assembly coupled to the device tip of the suturing device, the lead end rest assembly comprising:
      a lead end rest platform that extends from a proximal end to a distal end along a lead end rest axis, wherein the lead end rest axis forms an oblique angle with the shaft axis; and
      a first cavity formed in a portion of the lead end rest assembly, the first cavity defining a first ferrule holder configured to releasably hold a first ferrule coupled to a first portion of suture such that the needle tip of the first needle releasably couples with the first ferrule when the needle is displaced into the second needle position; and
   a pacemaker lead end that extends from a first end to a second end along a pacemaker lead end axis, the pacemaker lead end being removably disposed on the lead end rest platform such that the second end of the pacemaker lead end is disposed at or adjacent to the distal end of the lead end rest platform, wherein an electrode is coupled to a first portion of the pacemaker lead end, wherein the device tip is configured to be positioned adjacent a portion of tissue, and the pacemaker lead end is configured to be decoupled from the lead end rest platform and positioned on the portion of tissue such that the electrode contacts the portion of tissue.

2. The assembly of claim 1, further comprising a recess on the lead end rest platform configured to releasably receive the electrode of the pacemaker lead end.

3. The assembly of claim 1, further comprising an anchor tube guide on the device tip.

4. The device of claim 1, further comprising:
a first coupling suture tube configured to manage one or more ends of a first coupling suture configured to be coupled to a second portion of the pacemaker lead end; and
a second coupling suture tube configured to manage one or more ends of a second coupling suture configured to be coupled to a third portion of the pacemaker lead end.

5. The assembly of claim 1, the device tip further comprising a notch disposed along a portion of the device tip between the proximal end of the device tip and the distal end of the device tip, the notch extending from a first end to a second end and defining a tissue bite area that is configured to receive tissue that is to be sutured, wherein when the needle is displaced from the first needle position to the second needle position, the needle tip displaces from the first end of the notch to the second end of the notch across the tissue bite area.

6. The assembly of claim 5, the wherein the first end of the notch is a proximal end of the notch and the second end of the notch is a distal end of the notch.

7. The assembly of claim 1, wherein at least a portion of the first needle is curved.

8. The assembly of claim 1, wherein the pacemaker lead end includes at least one anchor suture hole.

9. The assembly of claim 8, further comprising:
an anchor suture, the anchor suture comprising a first portion that extends through a first one of the one or more anchor suture holes and a second portion coupled to at least one of the device tip and the shaft.

10. The assembly of claim 1, wherein the first cavity defining the first ferrule holder is disposed proximal to the proximal end of the lead end rest platform.

\* \* \* \* \*